(12) United States Patent
Benjamin et al.

(10) Patent No.: US 7,647,667 B2
(45) Date of Patent: *Jan. 19, 2010

(54) CHILD'S FRAGRANT CLEANING IMPLEMENT

(75) Inventors: Joyce Marie Benjamin, Mason, OH (US); Michael Wayne Mason, Cincinnati, OH (US); Jenna Mason, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 44 days.

This patent is subject to a terminal disclaimer.

(21) Appl. No.: 12/024,435

(22) Filed: Feb. 1, 2008

(65) Prior Publication Data

US 2008/0149504 A1 Jun. 26, 2008

Related U.S. Application Data

(63) Continuation of application No. 10/948,476, filed on Sep. 23, 2004, now Pat. No. 7,350,256, which is a continuation of application No. 10/737,236, filed on Dec. 16, 2003, now abandoned.

(51) Int. Cl.
*A47L 13/19* (2006.01)
*A47K 7/03* (2006.01)

(52) U.S. Cl. .................... 15/104.94; 15/227; 401/7

(58) Field of Classification Search ............ 15/104.93, 15/104.94, 227; 401/7; D28/63
See application file for complete search history.

(56) References Cited

U.S. PATENT DOCUMENTS

| 1,547,179 | A |   | 7/1925  | Martens |
|-----------|---|---|---------|---------|
| 2,187,163 | A | * | 1/1940  | Langer ................ 15/104.93 |
| 2,798,053 | A |   | 7/1957  | Brown |
| 2,831,854 | A |   | 4/1958  | Tucker et al. |
| 3,150,049 | A | * | 9/1964  | Emory ................. 424/447 |
| D218,079  | S | * | 7/1970  | Price .................... D28/63 |
| 3,711,889 | A |   | 1/1973  | Norton et al. |
| 3,755,560 | A |   | 8/1973  | Dickert et al. |
| 3,818,533 | A | * | 6/1974  | Scheuer ............... 15/104.93 |
| 3,862,472 | A |   | 1/1975  | Norton et al. |
| 3,902,509 | A | * | 9/1975  | Tundermann et al. ...... 433/142 |
| 3,929,678 | A |   | 12/1975 | Laughlin et al. |
| 3,952,867 | A | * | 4/1976  | McCord ................ 206/229 |
| 3,963,699 | A |   | 6/1976  | Rizzi et al. |
| 3,967,756 | A |   | 7/1976  | Barish |
| 3,982,302 | A |   | 9/1976  | Vaalburg |
| 3,982,659 | A |   | 9/1976  | Ross |
| 3,986,479 | A |   | 10/1976 | Bonk |
| 3,994,417 | A |   | 11/1976 | Boedecker |
| 4,004,323 | A |   | 1/1977  | Gotchel et al. |
| 4,005,195 | A |   | 1/1977  | Jandacek |

(Continued)

FOREIGN PATENT DOCUMENTS

EP          68516      *  1/1982

(Continued)

OTHER PUBLICATIONS

US 5,305,514, 04/1994, Letton et al. (withdrawn)

*Primary Examiner*—Mark Spisich
(74) *Attorney, Agent, or Firm*—John G. Powell

(57) ABSTRACT

A disposable child sized cleaning implement is provided. The disposable child sized cleaning implement is releasably carrying a personal care composition which comprises a fragrance composition.

10 Claims, 15 Drawing Sheets

U.S. PATENT DOCUMENTS

| | | | |
|---|---|---|---|
| 4,005,196 | A | 1/1977 | Jandacek |
| 4,057,669 | A | 11/1977 | McConnell |
| 4,097,965 | A | 7/1978 | Gotchel et al. |
| 4,130,915 | A | 12/1978 | Gotchel et al. |
| 4,135,024 | A | 1/1979 | Callahan et al. |
| 4,176,427 | A | 12/1979 | Neuenschwander |
| 4,189,896 | A | 2/1980 | Kolbach |
| 4,207,367 | A | 6/1980 | Baker |
| 4,233,212 | A | 11/1980 | Otoi et al. |
| 4,296,161 | A | 10/1981 | Kaiser et al. |
| 4,309,469 | A | 1/1982 | Varona |
| 4,397,754 | A * | 8/1983 | Collishaw et al. ........ 15/104.93 |
| 4,421,769 | A | 12/1983 | Dixon et al. |
| 4,471,881 | A | 9/1984 | Foster |
| 4,509,949 | A | 4/1985 | Huang et al. |
| 4,510,640 | A | 4/1985 | Omori |
| 4,517,360 | A | 5/1985 | Volpenhein |
| 4,518,772 | A | 5/1985 | Volpenhein |
| 4,523,348 | A | 6/1985 | Petrie |
| 4,599,379 | A | 7/1986 | Flesher et al. |
| 4,628,078 | A | 12/1986 | Glover et al. |
| 4,637,859 | A | 1/1987 | Trokhan |
| 4,682,942 | A | 7/1987 | Gotchel et al. |
| 4,741,855 | A | 5/1988 | Grote et al. |
| 4,797,300 | A | 1/1989 | Jandacek et al. |
| 4,835,206 | A | 5/1989 | Farrar et al. |
| 4,839,165 | A | 6/1989 | Hoppe et al. |
| 4,839,168 | A | 6/1989 | Abe et al. |
| 4,840,270 | A | 6/1989 | Caputo |
| 4,849,484 | A | 7/1989 | Heard |
| 4,892,372 | A | 1/1990 | Wenzel |
| 4,893,372 | A | 1/1990 | Wenzel |
| 4,960,764 | A | 10/1990 | Figueroa, Jr. et al. |
| 4,971,220 | A | 11/1990 | Kaufman et al. |
| 4,976,953 | A | 12/1990 | Orr et al. |
| 5,009,813 | A | 4/1991 | Watanabe et al. |
| 5,050,737 | A | 9/1991 | Joslyn |
| 5,055,216 | A * | 10/1991 | Johnson .................. 15/104.93 |
| 5,087,445 | A | 2/1992 | Haffey et al. |
| 5,100,660 | A | 3/1992 | Hawe et al. |
| 5,107,562 | A | 4/1992 | Dunn |
| 5,223,096 | A | 6/1993 | Phan et al. |
| 5,240,562 | A | 8/1993 | Phan et al. |
| RE34,584 | E | 4/1994 | Grote |
| 5,305,516 | A | 4/1994 | Letton et al. |
| 5,306,514 | A | 4/1994 | Letton et al. |
| 5,306,515 | A | 4/1994 | Letton et al. |
| 5,306,516 | A | 4/1994 | Letton et al. |
| 5,322,178 | A | 6/1994 | Foos |
| 5,366,104 | A | 11/1994 | Armstrong |
| 5,369,257 | A | 11/1994 | Gibbon |
| 5,412,634 | A | 5/1995 | Buchler et al. |
| 5,412,830 | A | 5/1995 | Girardot et al. |
| 5,487,884 | A | 1/1996 | Bissett et al. |
| 5,540,976 | A | 7/1996 | Shawver et al. |
| 5,542,566 | A | 8/1996 | Glaug et al. |
| 5,556,509 | A | 9/1996 | Trokhan et al. |
| 5,580,423 | A | 12/1996 | Ampulski et al. |
| 5,605,749 | A | 2/1997 | Pike et al. |
| 5,607,980 | A | 3/1997 | McAtee et al. |
| 5,647,506 | A | 7/1997 | Julius |
| 5,649,336 | A | 7/1997 | Finch et al. |
| 5,686,082 | A | 11/1997 | N'Guyen |
| 5,725,382 | A | 3/1998 | Walter et al. |
| 5,785,179 | A | 7/1998 | Buczwinski |
| 5,791,465 | A | 8/1998 | Niki |
| 5,833,998 | A | 11/1998 | Biedermann et al. |
| 5,839,842 | A | 11/1998 | Wanat et al. |
| 5,939,082 | A | 8/1999 | Oblong et al. |
| 5,955,417 | A | 9/1999 | Taylor |
| 6,024,970 | A | 2/2000 | Woodard |
| 6,032,319 | A * | 3/2000 | Garello .................... 15/229.11 |
| 6,092,690 | A | 7/2000 | Bitowft |
| 6,200,554 | B1 | 3/2001 | Yeoh et al. |
| 6,206,863 | B1 | 3/2001 | Skewes et al. |
| 6,238,678 | B1 | 5/2001 | Oblong et al. |
| 6,248,317 | B1 | 6/2001 | Snyder et al. |
| 6,257,785 | B1 | 7/2001 | Otten et al. |
| 6,269,969 | B1 | 8/2001 | Huang |
| 6,269,970 | B1 | 8/2001 | Huang |
| 6,280,751 | B1 | 8/2001 | Fletcher et al. |
| 6,292,949 | B1 | 9/2001 | Chang |
| 6,296,144 | B1 | 10/2001 | Tanaka |
| 6,315,114 | B1 | 11/2001 | Keck |
| 6,322,801 | B1 | 11/2001 | Lorenzi et al. |
| 6,335,312 | B1 | 1/2002 | Coffindaffer et al. |
| 6,401,968 | B1 | 6/2002 | Huang |
| 6,412,634 | B1 | 7/2002 | Telesca |
| 6,440,437 | B1 | 8/2002 | Krzysik et al. |
| 6,501,002 | B1 | 12/2002 | Roe et al. |
| 6,506,394 | B1 | 1/2003 | Yohiaoui et al. |
| 6,630,175 | B1 | 10/2003 | Shapiro et al. |
| 6,669,387 | B2 | 12/2003 | Gruenbacher et al. |
| 6,726,386 | B1 | 4/2004 | Gruenbacher et al. |
| 6,780,825 | B2 | 8/2004 | Piterski et al. |
| 7,021,483 | B2 | 4/2006 | Tack et al. |
| 7,152,737 | B2 | 12/2006 | Chin |
| 7,188,746 | B2 | 3/2007 | Zethoff et al. |
| 2002/0064323 | A1 | 5/2002 | Chin |
| 2002/0177535 | A1 | 11/2002 | Diterski et al. |
| 2002/0178482 | A1 | 12/2002 | Samuelsson et al. |
| 2003/0130636 | A1 | 7/2003 | Brock et al. |
| 2003/0140439 | A1 * | 7/2003 | Durden et al. ........... 15/104.93 |
| 2003/0143263 | A1 * | 7/2003 | Durden et al. ............... 424/443 |
| 2003/0190337 | A1 | 10/2003 | Bissett |
| 2003/0215486 | A1 | 11/2003 | Berry et al. |
| 2003/0217425 | A1 | 11/2003 | Datta et al. |
| 2004/0022833 | A1 * | 2/2004 | Hartwig et al. ............. 424/443 |
| 2004/0118530 | A1 | 6/2004 | Kressner et al. |
| 2004/0204333 | A1 | 10/2004 | Dobrin et al. |
| 2004/0244132 | A1 * | 12/2004 | Ouellette et al. ............... 15/227 |
| 2005/0042261 | A1 | 2/2005 | Hasenoehrl et al. |
| 2005/0125877 | A1 | 6/2005 | Benjamin et al. |
| 2005/0125923 | A1 | 6/2005 | Benjamin et al. |
| 2005/0125924 | A1 | 6/2005 | Benjamin et al. |
| 2005/0129743 | A1 | 6/2005 | Benjamin et al. |
| 2005/0150784 | A1 | 7/2005 | Sanchez et al. |

FOREIGN PATENT DOCUMENTS

| | | |
|---|---|---|
| EP | 0 068 516 A1 | 1/1983 |
| EP | 228868 | 7/1987 |
| FR | 2 813 777 A | 3/2002 |
| WO | WO 97/38598 A1 | 10/1997 |
| WO | WO 97/39733 A1 | 10/1997 |
| WO | WO 99/55213 | 11/1999 |
| WO | WO 00/27268 | 5/2000 |
| WO | WO 01/08641 A | 2/2001 |
| WO | WO 02/14172 | 2/2002 |
| WO | WO 03/000106 A1 | 1/2003 |
| WO | WO 2004/080256 A1 | 9/2004 |
| WO | WO 2004/080257 A1 | 9/2004 |
| WO | WO 2004/080258 A1 | 9/2004 |

* cited by examiner ized children. The need also remains for disposable cleaning products which are easy to use, suitable for use by and attractive and appealing to children, of different ages, all sizes and/or stages of development, which can reduce any stress and tension a child may have during the use of a consumer product.

CHILD'S FRAGRANT CLEANING IMPLEMENT

CROSS REFERENCE TO RELATED APPLICATION

This application is a continuation of application Ser. No. 10/948,476, filed Sep. 23, 2004, now U.S. Pat. No. 7,350,256, which is continuation of application Ser. No. 10/737,236, filed Dec. 16, 2003, now abandoned.

COPYRIGHT NOTICE

A portion of the disclosure of this patent document contains material which is subject to copyright and/or trademark protection. The copyright and trademark owner has no objection to the facsimile reproduction by anyone of the patent document or the patent disclosure, as it appears in the Patent and Trademark Office patent file or records, but otherwise reserves all copyright and trademark rights whatsoever.

FIELD OF INVENTION

A disposable child sized cleaning implement is provided. The disposable child sized cleaning implement is releasably carrying a personal care composition which comprises an aromatherapy adjuvant.

BACKGROUND OF THE INVENTION

Consumer products, such as, cleansing and conditioning products as well as household consumer cleaning products, have traditionally been marketed in a variety of forms such as bar soaps, creams, foams, sprays, liquids, powders, lotions, and gels. Typically, these products must satisfy a number of criteria to be acceptable to consumers. These criteria include effectiveness, skin feel, mildness to skin, suitability for use in the consumer's household, and appearance. Typically these consumer products comprise a benefit composition in some form.

It is highly desirable to deliver benefit compositions from a disposable substrate. Disposable products are convenient because they obviate the need to carry or store cumbersome bottles, bars, jars, tubes, and other forms of clutter associated with consumer products. Disposable products are also a more sanitary alternative to the use of a sponge, washcloth, or other cleansing implement intended for extensive reuse, because such implements can develop bacterial growth, unpleasant odors, and other undesirable characteristics related to repeated use.

It can now be appreciated that using consumer products involves many aspects for both the child and the caregiver, especially for the child incapable of reading. Some of these aspects affect children differently, or may not even be a factor for a particular child. It is this uniqueness of each individual child that presents a major challenge for both the child and the caregiver. If any of these aspects are unsuccessful, the child's progress in learning how to, for example bathe or clean properly can be unnecessarily delayed due to numerous failures and frustrations. In the past reusable washcloths and sponges have been made in various shapes, such as puppets and with child appealing graphics, in order to make the use of these products fun and enjoyable. However, these reusable products still suffer from the problems associated with repeated use, i.e. bacterial growth, unpleasant odors, and other undesirable characteristics related to extensive reuse. One the other hand, while disposable products side step this problem of extensive reuse, no effort has been made to make disposable products more appealing to children.

Furthermore, a child may at this age, desire privacy and independence. This may be indicated when, for example the child closes a bathroom door when bathing, when in the past an open door was never a concern. If the caregiver needs to assist the child, there can be a conflict of emotion for the child that may be obstructive to the bathing process. There needs to be some way of providing reducing the stress and tension of the child which may be associated with the use of a consumer article, especially during the bathing process.

The problem remains that there is no disposable cleaning articles, products or system available for children of all ages and sizes, which can be easily handled and the method of utilizing easily understood, by the child. The need also remains for disposable cleaning products which are easy to use, suitable for use by and attractive and appealing to children, of different ages, all sizes and/or stages of development, which can reduce any stress and tension a child may have during the use of a consumer product.

SUMMARY OF THE INVENTION

A first aspect of the present invention provides, a disposable child sized cleaning implement comprising:
 (a) a personal care composition, wherein the personal care composition comprises an aromatherapy adjuvant and the disposable child sized cleaning implement is releasably carrying the personal care composition; and
 (b) a child graphic disposed on the disposable cleaning implement A second aspect, the present invention provides, a non-woven mitt adapted to fit on a child's hand, the mitt comprising:
 (a) a personal care composition, wherein the personal care composition comprises an aromatherapy adjuvant and the disposable nonwoven child's cleansing mitt is releasably carrying the personal care composition; and
 (b) a child graphic disposed on the disposable nonwoven child's cleansing mitt;

A third aspect, the present invention provides, a disposable nonwoven mitt adapted to fit on a child's hand, the mitt comprising:
 (a) first and second nonwoven sheet members in an overlying relationship, the members defining an interior volume for receiving the child's hand, each of the first and second nonwoven sheet members including an exterior surface, having an opposing interior surface, a top edge, a bottom edge opposing the top edge, and first and second opposed side edges, the first and second nonwoven sheet members being permanently secured to each other along the periphery of the top edge and both of the first and second opposed side edges, with the bottom edges being unsecured so as to provide a substantial access opening to the interior volume for readily inserting the child's hand therein;
 (b) a personal care composition, wherein the personal care composition comprises an aromatherapy adjuvant and at least one of the first and second sheet members is releasably carrying said personal care composition; and
 (c) a child graphic disposed on at least one of the first and second sheet members.

All documents cited are, in relevant part, incorporated herein by reference; the citation of any document is not to be construed as an admission that it is prior art with respect to the present invention. It should be understood that every limit given throughout this specification will include every lower, or higher limit, as the case may be, as if such lower or higher limit was expressly written herein. Every range given throughout this specification will include every narrower range that falls within such broader range, as if such narrower ranges were all expressly written herein. All percentages, ratios and proportions are by weight, and all temperatures are in degrees Celsius (° C.), unless otherwise specified. All measurements are in SI units unless otherwise specified.

BRIEF DESCRIPTION OF THE DRAWINGS

The above-mentioned and other features and objects of this invention and the manner of attaining them will become more apparent, and the invention itself will be better understood by reference to the following description of the invention taken in conjunction with the accompanying drawings, wherein.

DETAILED DESCRIPTION

Figure 1:
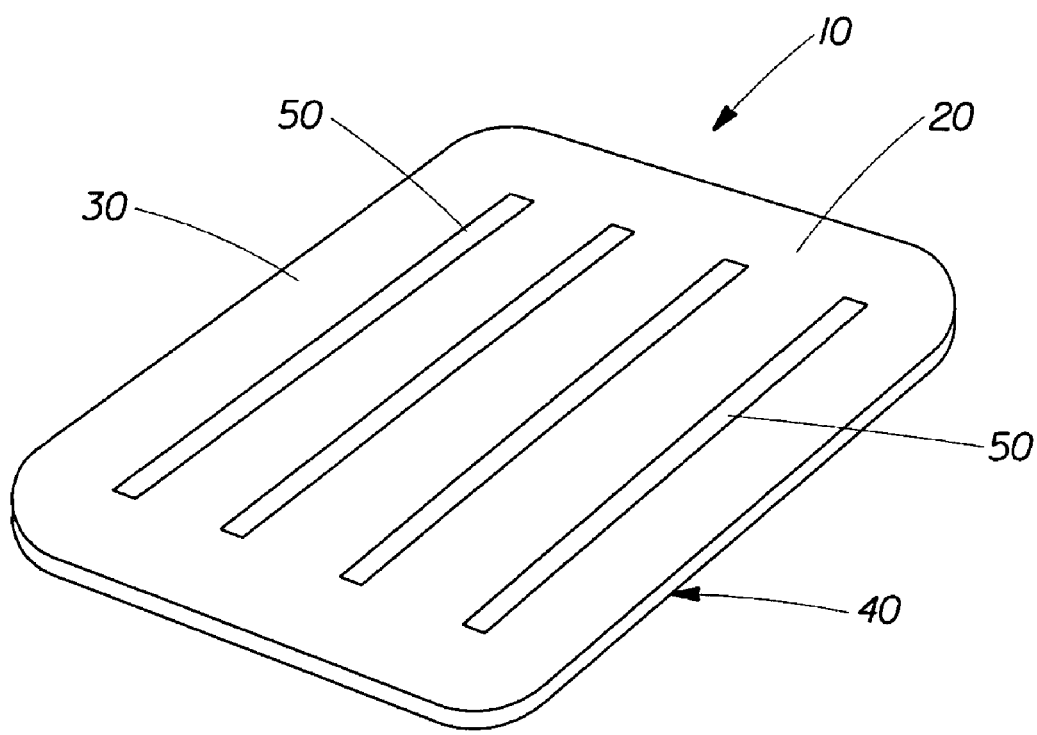
FIG. 1 illustrates one embodiment of a disposable cleaning implement.

The instant implements, and methods are suitable for use by children in personal cleansing. Due to the ease and simple method of use very young children are able to clean themselves, to an extent independently, with the instant invention. The incorporation of an aromatherapy adjuvant reduces stress, relaxes, calms and uplifts the child, and possibly any care giver present while the implement is in use.

Definitions

As used herein the abbreviation "gsm" means "grams per square meter".

As used herein, "disposable" is used in its ordinary sense to mean an implement that is disposed or discarded after a limited number of usage events, preferably about 2 or less, and more preferably about 1 entire usage events.

The term "releasably carrying" means that a composition is contained in and/or on a implement, mitt, nonwoven member and/or parts thereof and is readily releasable from the implement, mitt, nonwoven member and/or parts thereof by application of water and/or application of some force thereto, for example, wringing the disposable child sized implement, wiping a child, or immersing part or all of the disposable child sized implement in water.

As used herein, the term "comprising" means that the various components, ingredients, or steps, can be conjointly employed in practicing the present invention. Accordingly, the term "comprising" is open-ended and encompasses the more restrictive terms "consisting essentially of" and "consisting of." Other terms may be defined as they are discussed in greater detail herein.

As used herein, the term "graphic" means any design, shape, pattern, or the like that is or becomes visible on an implement, and specifically includes text messages, that include one or more alphanumeric symbol, pictorial images that consist of one or more pictures, and combination thereof.

As used herein, the term "child graphic" means any graphic which appeals to a child such that the child will want to possess and/or interact with the implement in some fashion, preferably the typical use to which the implement is put. The child graphic can be aesthetically pleasing, objectively and/or subjectively desirable to any child. The child graphic can in addition be aesthetically pleasing and/or objectively desirable to a child's caregiver. Typically, any child graphic can be supportive and/or encouraging of a child. This support and/or encouragement can be of any suitable subject matter, such as but not limited to, providing advice to the child on any of a range of diverse subjects such as: education e.g. numbers, letters, words, shapes and the like, child appropriate facts and factoids, and combinations thereof; sports and games; jokes, rhymes, limericks humorous stories and the like; social and religious issues, such as but not limited to, sharing and caring, bullying, civics, and the like; safety, such as but not limited to, stranger danger, road safety, hygiene, (i.e., hand washing, bottom wiping and the like); and combinations thereof. One such suitable subject matter of the support and/or encouragement can be with respect to the child's desire to possess and/or interact with the implement in some fashion.

A child graphic can comprise a character or characters. This character may be shown using the implement in an appropriate fashion. The child graphic may additionally include one or more secondary images of the character or characters or parts thereof, performing one or more steps associated with using the implement. Illustrative examples of such step(s) include, but are not limited to: preparation step(s) associated with using the implement, such as but not limited to accessing the implement and the like; lathering the implement and the like; using the implement; and/or disposing of the spent implement and/or optional container and the like.

Without wishing to be limited to the specific embodiments listed, suitable examples of child graphics may include: a character graphic operating a vehicle, and another child graphic comprising stars, balls, or the like; a character graphic jumping rope, and another child graphic comprising flowers; a character graphic feeding or nurturing and animal, and another child graphic comprising letters of the alphabet; a character graphic holding or using a racquet, bat, glove, other sporting equipment, or illustrated on a sporting field, or the like, and another child graphic comprising objects that are not associated with sports, sporting equipment or the like; a character graphic holding a butterfly net or the like and another child graphic comprising objects that are not associated with butterflies or the like; a character graphic holding a fishing pole, sitting in a boat or the like and another child graphic comprising objects that are not associated with fish, inflatable water toys or the like; a character graphic holding flowers, plants, gardening tools or the like and another child graphic comprising objects that are not associated with flowers, plants or gardening; a character graphic comprising a pet or other animal or an anthropomorphous image feeding, training or nurturing an animal and another child graphic comprising objects that are not associated with pets, animals, animal food, pet toys, or the like; a character graphic playing in a specific environment such as a doll house, barn yard or the like and optionally another child graphic; a character graphic holding or using a telescope or the like and another child graphic comprising objects such as stars, planets or the like; a character graphic comprising a racecar and another child graphic associated with racing; a character graphic comprising a submarine and another child graphic comprising objects associated with fish, bubbles, shells or the like; or other suitable graphics.

The child graphic may vary depending upon the age and/or developmental stage of the child. Typically, this would mean when a graphic is intended for a younger child, typically of approximate age 3 or 4, the graphics will be simpler in nature and comprise bright colors, and typically be easily identifiable and relatable to by a child of that age. The selection of available colors as well as the possible complexity of the child graphics may be increased as the age of the intended child increases. Typically, the older the intended child the more colors, especially subtle colors shades etc, and complex images are available for use on the implement.

The child graphic may vary depending upon the gender of the intended child; for example, the child graphic may comprise colors and images which are appealing to girls, such as pinks and images of dolls, rabbits, doll houses and the like or the child graphic may comprise colors and images which are appealing to boys, such as blues and rockets, construction machines, trains and the like. Alternatively, the child graphic may comprise colors and images which are gender neutral and are appealing equally to girls and boys such as purples and greens and cartoon characters, or the child graphic may comprise colors and images which comprise parts which are appealing to boys, parts which are appealing to girls and is overall appealing to both boys and girls.

The term "unrelated in subject matter" is used herein to mean that one graphic is not the same as or is not associated with the subject matter of another graphic. The subject matter relationship or lack thereof can be between two or more text messages, between two or more pictorial images, or between a combination of one or more text messages and one or more pictorial images. The term "text message" means a graphic consisting of one or more alphanumeric symbols, and the term "pictorial image" means a graphic consisting of one or more pictures. The terms "text image" and "pictorial image" are mutually exclusive as used herein.

By way of illustration and without wishing to be limited to the enumerated examples, two pictorial images are considered unrelated in subject matter where the images: illustrate items that are neither identical nor different sizes, shapes, or colors of a common object; illustrate two objects that are not commonly associated with one another, such as an animal and a building block, a jump rope and a flower, a car and a star, a letter of the alphabet and a water toy, a fish and an apple, illustrate items used in unrelated activities, such as items used in sporting activities and items used in gardening activities, or other unrelated activities; or the like. Similarly, two text messages are considered unrelated in subject matter where the messages: are neither identical nor jointly form a sentence, thought, or action; refer to two items that are not commonly associated with one another, such as "ball" and "flower," "fish" and "pencil," "car" and "ghost," or other such unrelated words; or the like. Likewise, a text message and a pictorial image are considered to be unrelated in subject matter where the text does not name, define, describe or otherwise relate to the image.

As used herein, the phrase "related in subject matter" refers to the situation where the subject matter of one graphic is the same as or is associated with the subject matter of another graphic. By way of example, two pictorial images are considered related in subject matter where the images are identical; separately illustrate different sizes, shapes, colors of a common object; each illustrate one and the other of two objects that are commonly associated with one another, such as the moon and stars, a body of water and water toys, a sandbox and suitable toys, a baseball bat and ball, a barn and animals, or the like; illustrate different items used in a particular activity, such as a sporting activity, a gardening activity or the like; jointly illustrate geometrically mating or engaging elements such as a triangle and a triangularly-shaped aperture, or two halves of a zipper; each illustrate one part of a multipart picture; or the like. Similarly, two text messages are considered related in subject matter where the messages: are identical; jointly form a sentence, thought, or action such as "jump" and "up"; each refer to one and the other of two items that are commonly associated with one another, such as but not limited to "bat" and "ball; jointly present a question and answer; or the like. Likewise, a text message and a pictorial image are considered to be related in subject matter where the text names, defines or describes the image; or the like.

The term "disposed on" and variations thereof are intended to mean that one element can be integral with another element, or that one element can be a separate structure bonded to or placed with or placed near another element. For example, graphics can be formed or applied directly or indirectly to a surface of a substrate, such as but not limited to, the nonwoven sheet member, any surface of a container, or other variations or combinations thereof. In particular embodiments, graphics may be printed, sprayed, or otherwise applied directly on a layer of the nonwoven sheet member.

(b) Disposable Cleaning Implement

Referring to FIG. 1, there is illustrated one possible embodiment of a disposable child sized cleaning implement (or disposable cleaning implement, or disposable implement, or implement) 10, in accordance with the present invention. The disposable cleaning implement 10 comprises a nonwoven sheet member, having a first surface 30, and an opposing second surface 40.

The disposable cleaning implement 10 also comprises a personal care composition 50. The disposable cleaning implement 10 is releasably carrying the personal care composition 50 on its first surface 30. In one embodiment of the present invention the personal care composition may be present on a part of the disposable cleaning implement 10, such as but not limited to, the first surface 30 in the form of stripes, spots, geometric patterns, non-geometric patterns or in a random distribution. In an alternative embodiment, the personal care composition 50 may be present on the entire first surface 30 of the disposable cleaning implement 10. In another an alternative embodiment, not shown, the personal care composition may be present in the interior of the disposable cleaning implement, and/or the first surface of the disposable cleaning implement.

It is to be understood that while in FIG. 1 the first surface 30 of the disposable cleaning implement 10 is releasably carrying the personal care composition 50 in other embodiments of the present invention the opposing second surface 40 of the disposable cleaning implement 10 may be releasably carrying the personal care composition. There is no restriction as to which surface of the disposable cleaning implement is releasably carrying the personal care composition. It is even possible that all of the surfaces of the disposable cleaning implement be releasably carrying the personal care composition. Furthermore, the personal care composition may be carried on any surface, and/or interior of a disposable cleaning implement as long as the disposable cleaning implement is releasably carrying it.

In one optional embodiment the disposable cleaning implement is a disposable nonwoven mitt (or nonwoven mitt, or mitt or mitten) adapted to fit on a child's hand. In one optional embodiment the nonwoven mitt may optionally comprises a first and second complementary nonwoven sheet members. Nonlimiting examples of such child's cleansing mitts may be found in FIGS. 2 and 4.

Figure 2:
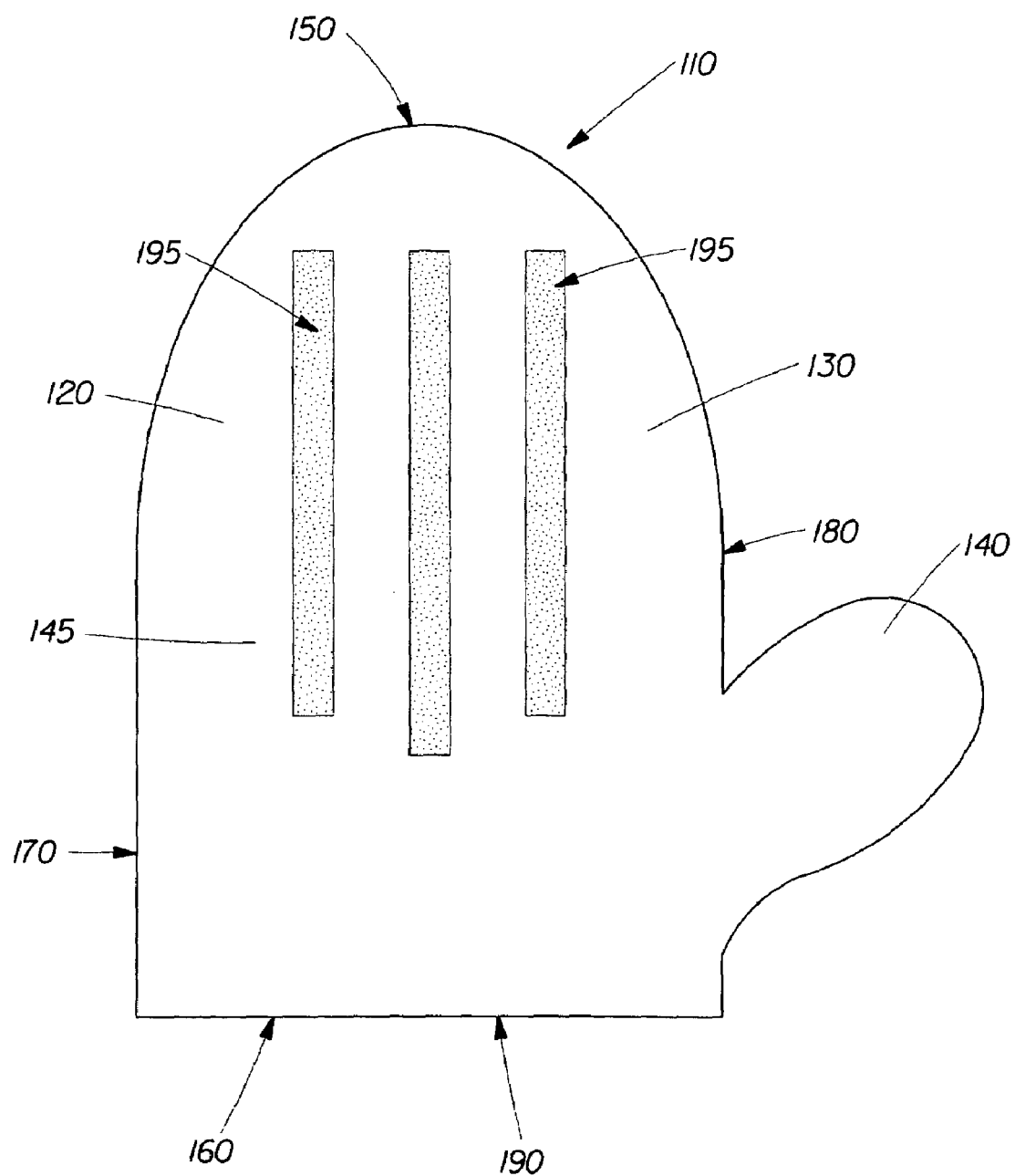
FIG. 2 illustrates one embodiment of a disposable nonwoven child's cleansing mitt.

In FIG. 2, there is illustrated one possible embodiment of a nonwoven child's cleansing mitt 110, in accordance with the present invention. The mitt 110 comprises a first nonwoven sheet member 120, which has an exterior surface 130, an interior surface, a top edge 150, a bottom edge 160, a first side edge 170 and a second side edge 180. The first nonwoven sheet member 120, together with a substantially complementary second nonwoven sheet member, which are in an overlying relationship, define an interior volume which is accessed by the user's hand (i.e., a child) via opening 190.

The interior volume of mitt 110 is divided into two parts, one part for the child's thumb 140 and one part for the remainder of the child's hand 145.

The mitt 110 also comprises a personal care composition 195. The first nonwoven sheet member 120 is releasably carrying the personal care composition 195 on its exterior surface 130. In one embodiment of the present invention the personal care composition may be present on a part of the first nonwoven sheet member 120, such as, but not limited to, the exterior surface 130 in the form of stripes, spots, geometric patterns, non-geometric patterns or in a random distribution. In an alternative embodiment, the personal care composition 195 may be present on the entire exterior surface 130 of the first nonwoven sheet member 120. In another an alternative embodiment, not shown, the personal care composition may be present in the interior of the first nonwoven sheet member, and/or the exterior surface of the nonwoven sheet member.

Figure 3:
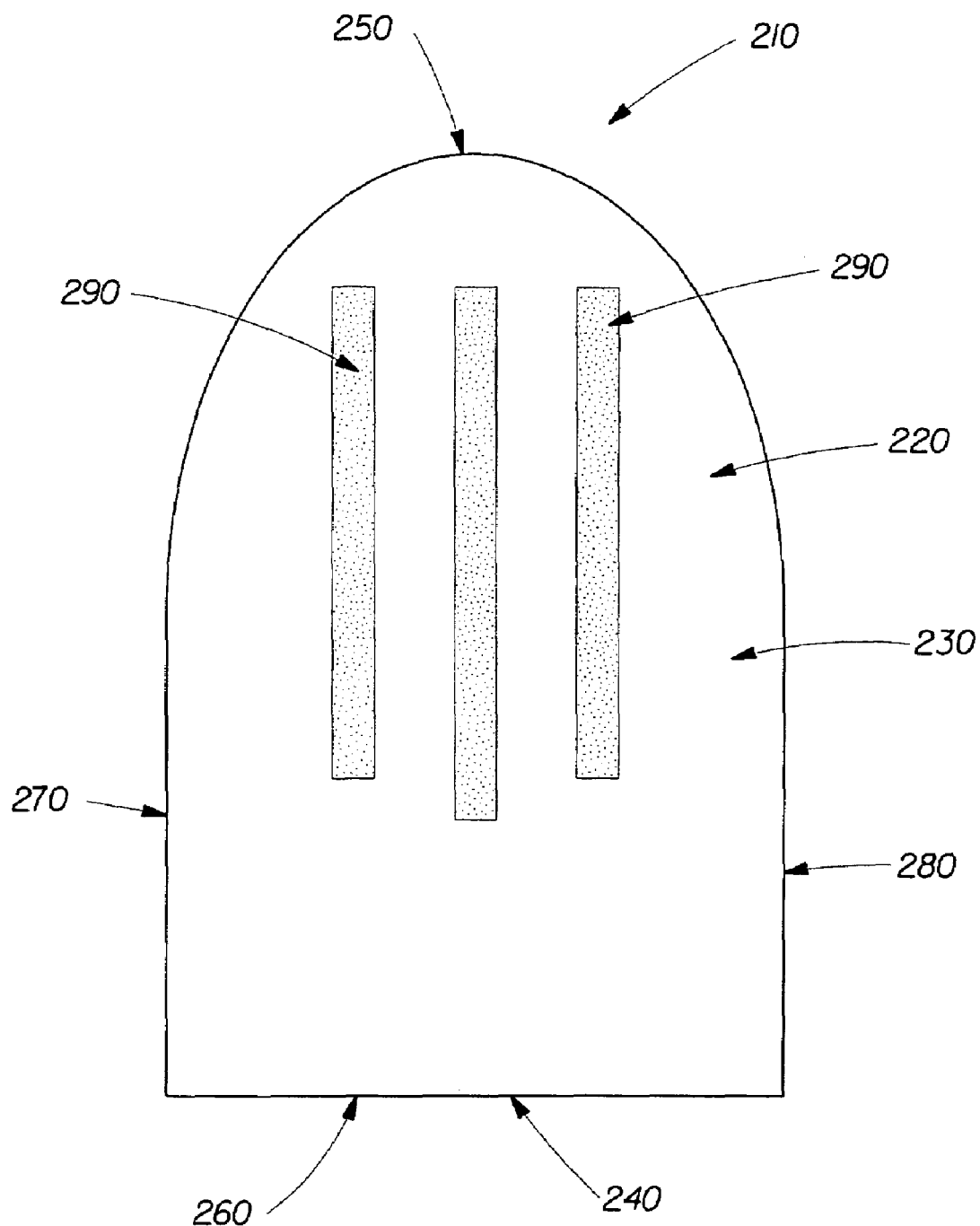
FIG. 3 illustrates another alternative embodiment of a disposable nonwoven child's cleansing mitt.

It is to be understood that while in FIG. 3 the exterior surface 130 of the first nonwoven sheet member 120 is releasably carrying the personal care composition 195 in other embodiments of the present invention the second nonwoven sheet member may be releasably carrying the personal care composition. There is no restriction as to which of the first nonwoven sheet member and the second nonwoven sheet member is releasably carrying the personal care composition. It is even possible that both the first and second nonwoven sheet members be releasably carrying the personal care composition. Furthermore, the personal care composition may be carried on the exterior surface, interior, and/or interior surface of a nonwoven member as long as the nonwoven member is releasably carrying it.

Referring to FIG. 3, there is illustrated another possible embodiment of a mitt 210, in accordance with the present invention. The mitt 210 comprises a first nonwoven sheet member 220, which has an exterior surface 230, an interior surface, a top edge 250, a bottom edge 260, a first side edge 270 and a second side edge 280. The first nonwoven sheet member 220, together with a complementary second nonwoven sheet member, which are in an overlying relationship, define an interior volume which is accessed by the user's hand via opening 240.

The mitt 210 also comprises a personal care composition 290. The first nonwoven sheet member 220 is releasably carrying the personal care composition 290 on its exterior surface 230. In one embodiment of the present invention the personal care composition may be present on a part of the first nonwoven sheet member 220, such as but not limited to, the exterior surface 230 in the form of stripes, spots, geometric patterns, non-geometric patterns or in a random distribution. In an alternative embodiment, the personal care composition 290 may be present on the entire exterior surface 230 of the first nonwoven sheet member 220. In another an alternative embodiment, not shown, the personal care composition may be present in the interior of the first nonwoven sheet member, and/or the exterior surface of the nonwoven sheet member.

It is to be understood that while in FIG. 3 the exterior surface 230 of the first nonwoven sheet member 220 is releasably carrying the personal care composition 290 in other embodiments of the present invention the second nonwoven sheet member may be releasably carrying the personal care composition. There is no restriction as to which of the first nonwoven sheet member and the second nonwoven sheet member is releasably carrying the personal care composition. It is even possible that both the first and second nonwoven sheet members be releasably carrying the personal care composition. Furthermore, the personal care composition may be carried on the exterior surface, interior, and/or interior surface of a nonwoven member as long as the nonwoven member is releasably carrying it.

In one optional embodiment of the present invention the disposable cleaning implement of the present invention may comprise an attachment means to snugly attach the disposable cleaning implement to the child's hand. The attachment means may be any suitable means for permitting a removable attachment of the disposable cleaning implement of the present invention to a child's hand. Suitable adjustment means, include but are not limited to, hook and loop fasteners such as Velcro® and the like, elastic members, buttons, fasteners, tabs, resealable tape, belts, clips, refastenable adhesives, and combinations thereof.

In one optional embodiment of the present invention when the disposable cleaning implement is a child's cleansing mitt, it may comprise an adjustment means to snugly accommodate different child hand sizes. The adjustment means may be any means suitable for permitting a variation in the size of an interiorly defined volume, to snugly accommodate different child hand sizes. Suitable adjustment mechanism, include but are not limited to, include, hook and loop fasteners such as Velcro® and the like, gussets, cinches, elastic members, elastic strands, buttons, fasteners, tabs, resealable tape, belts, clips, refastenable adhesives, and combinations thereof.

In an alternative embodiment of the present invention the material, or a portion of the material, which comprises the disposable cleaning implement is selected such that it, will adhere, cling or stick to the child's hand prior to and during use. For example, the mitt 210 of FIG. 3, may optionally comprise in its interior surface material that will adhere, stick or cling to the child's hand prior to and during use. This optional adhesion may be achieved in a variety of ways, including but not limited to, adhesive, friction, electrostatic attraction, conformation or constriction of the disposable cleaning implement or a portion thereof, to the shape of the child's hand when wet, fluid between the child's hand and the material and combinations thereof. Suitable material for this optional adhesion, include but do not limited to, adhesive, polyolefin films such as films comprising polyethylene and/or polypropylene, and combinations thereof.

The material of which disposable cleaning implements are made from should be strong enough to resist tearing during normal use, yet still provide softness to the child's tender skin. Additionally, the material should be water insoluble, or at least capable of retaining its form for the duration of the child's cleansing experience.

In one embodiment of the instant invention the disposable cleaning implements comprise a mixture of natural fibers and synthetic fibers. In alternative embodiments of the present invention the disposable cleaning implements may wholly comprise natural fibers, while in other alternative embodiments still may wholly comprise synthetic fibers.

In one embodiment of the present invention when the disposable cleaning implement comprises two nonwoven sheet members each nonwoven sheet member is made of material which is different to that of the other nonwoven sheet member. In another alternative embodiment of the present invention when the disposable cleaning implement comprises two nonwoven sheet members the two nonwoven sheet members are made of the same material.

Suitable natural fibers include but are not limited to cellulosic fibers, such as wood pulp fibers, cotton, and rayon. Suitable synthetic fibers include fibers commonly used in textiles, including but not limited to, polyester and polypropylene fibers polyethylene, polyether, PET, and combinations thereof. It is also possible to use bicomponent polymers, or simply bico or sheath polymers. These bico polymers can be used as a component fiber of the nonwoven sheet member, and/or they may be present to act as a binder for the other fibers present in the nonwoven material. Suitable nonwovens with good softness include, but are not limited to, nonwoven materials comprising polypropylene, polyethylene, cellulose, rayon, polyether, PET, bicomponent polymers, and combinations thereof.

Various forming methods can be used to form the disposable cleaning implements, and/or the nonwoven sheet members. For instance, the disposable cleaning implements can be made by nonwoven dry forming techniques, such as airlaying, or alternatively by wet laying, such as on a papermaking machine, of a continuous web out of which the cleansers are made. Other nonwoven manufacturing techniques, including but not limited to, techniques such as adhesive bonding, melt blown, spunbonded, carding, needle punched, hydroentanglement and lamination methods may also be used.

The disposable cleaning implements of the present invention may be subjected to various treatments, such as but not limited to, physical treatment, such as zone activation, ring rolling SELFing and the like; chemical treatment, such as rendering part or all of the disposable cleaning implements hydrophobic, and/or hydrophilic, and the like; thermal treatment, such as softening of fibers by heating, thermal bonding and the like; and combinations thereof.

The disposable child sized implement may be of any size which is suitable for use by a child. Furthermore, the implement may be of a size to be used by a specific developmental age of child, such as 4, or 7 and the like. Alternatively, the disposable child sized implement may be of a size which is suitable for use by any child. Typically, the size of the disposable child sized implement will depend upon many factors such as dexterity and hand eye coordination of the child, size of the child's hand, gender, ethnicity, and the like. Anthropomorphic data on child hand sizes may be found in Consumer Safety CHILDATA: Handbook of Child Measurements (Beverly Norris & John Wilson, June 1985). Furthermore, the dimensions and size of the disposable child sized implement will depend upon the shape, weight and composition of the nonwoven sheet member, the retaining aid used and the intended use of the implement. Typically, a substantially rectangular disposable child sized implement will have a length of from about 50 mm to about 200 mm, a width of from about 50 mm to about 150 mm and a thickness of about 0.01 mm to about 30 mm. Alternatively, the area of one side of the disposable child sized implement, such as but not limited to the side comprising the benefit composition, has an area of from about 100 $mm^2$ to about 30,000 $mm^2$.

The disposable child sized implement may also optionally comprise a usage indicator. This optional usage indicator provides a means for the child to readily identify correct usage of the implement, when all or a portion benefit composition has been released from any nonwoven member present, and/or they have used the implement for a sufficient amount of time. The usage indicator may be a separate feature or it may be part of the benefit composition, or it may be a part of a child graphic, or a child graphic when more than one child graphic is present. This type of usage indicator is described further herein. Other suitable usage indicators include, but are not limited to, pH (e.g., at a specific pH or pH range a noticeable event occurs such as color change, noise generation or cessation and the like and combinations thereof), temperature (e.g., the implement may feel warm cold for its intended use and then revert to ambient temperature, or change temperature form ambient after a period of time), time (e.g., the indicator may change size shape, color etc after a time period since it was exposed to water air, oxygen, shear or other force and the like), and the like and combinations thereof. In one optional embodiment the usage indicator provides a visual signal during use of the implement at least a portion of the benefit composition has been released, such as but not limited to, from a nonwoven member.

When present, the type of optional usage indicator will depend upon many factors, such as but not limited to, size and type of material present in implement, benefit composition, intended use of the implement, age of child using the implement the child graphic used and the like. In any event the selection of the usage indicator, when present, should not typically not be in isolation from the other elements, such as but not limited to, any character graphic, for example a usage indicator which changes to red, is probably not suitable for younger children because of the possible distress it may possibly cause to a care giver, who thinks the child is possibly hurt, and/or to the child who may think the character is possibly hurt, or a use indictor which changes to green may possibly appear to be gross and slimy to care givers and/or girls (but which may conversely possibly be fascinating and very appealing to boys). In any event selection of usage indicator will depend upon many factors and should not typically be made in isolation of the other components of the implement.

It is also within the scope of the present invention that the disposable cleaning implements, or components thereof, such as but not limited to nonwoven sheet members when present, may comprise laminates of two or more substrates or webs. Commercially available laminates, or purpose built ones would be within the scope of the present invention. Additionally, the disposable cleaning implements, or components thereof and/or regions thereof may be flat or textured. The formation of textured disposable cleaning implements, and laminates forms no part of this invention. The following discussion is for convenience of formulation, but is not intended to limit the type of disposable cleaning implements used herein.

In one embodiment of the present invention the surface of disposable cleaning implements is essentially flat. In another embodiment of the present invention the surface of the cleanser may optionally contain raised and/or lowered portions. These can be in the form of logos, indicia, trademarks, geometric patterns, images of the surfaces that the child's cleansing mitt is intended to clean (i.e., child's body, face, etc.). They may be randomly arranged on the surface of the disposable cleaning implements or be in a repetitive pattern of some form. They may be on one or both of the sides or surfaces of the disposable cleaning implements. In one embodiment one of the nonwoven sheet members contains a repetitive pattern or alternating raised and lowered portions of the substrate. This variation in or on the surface of one side of the disposable cleaning implement may be included to, for example, convey to the child or a caregiver information on the disposable cleaning implements intended use, how a child is to place the child's cleansing mitt on the child's hand, which brand or type of disposable cleaning implement they are using is or even to aid in cleaning of the child.

In another embodiment of the present invention the disposable cleaning implements is biodegradable. For example the cleanser could be made from a biodegradable material, such as a polyesteramide.

In one optional embodiment the disposable cleaning implement is a child's cleansing mitt, and comprises first and second substantially complementary nonwoven sheet members. The first and second complementary nonwoven sheet members may be joined or bonded together in any suitable fashion. For example, the first and second nonwoven sheet members may be joined by ultrasonically bonding, sewing, adhesively, mechanically bonding, fusion bonding, heat or thermal bonding and combinations thereof. The first and second nonwoven sheet members are joined at their respective first, second and top edges. The bottom edges may be either totally unbonded or partially bonded. Any such partial bond will not restrict a child from wearing the mitt, and may aid in securing the mitt to the child's hand.

Additional information on materials which are suitable for use as the disposable cleaning implements, child's cleansing mitt, nonwoven sheet members and/or other components thereof can be found in the following patents: U.S. Pat. No. 3,862,472 issued Jan. 28, 1975; U.S. Pat. No. 3,982,302 issued Sep. 28, 1976; U.S. Pat. No. 4,004,323 issued Jan. 25, 1977; U.S. Pat. No. 4,057,669 issued Nov. 8, 1977; U.S. Pat. No. 4,097,965 issued Jul. 4, 1978; U.S. Pat. No. 4,176,427 issued Dec. 4, 1979; U.S. Pat. No. 4,130,915 issued Dec. 26, 1978; U.S. Pat. No. 4,135,024 issued Jan. 16, 1979; U.S. Pat. No. 4,189,896 issued Feb. 26, 1980; U.S. Pat. 4,207,367 issued Jun. 10, 1980; U.S. Pat. No. 4,296,161 issued Oct. 20, 1981; U.S. Pat. 4,309,469 issued Jan. 25, 1982; U.S. Pat. No. 4,682,942 issued Jul. 28, 1987; U.S. Pat. Nos. 4,637,859; 5,223,096; 5,240,562; 5,556,509; and 5,580,423 and U.S. patent application No. US2003/0217425 Published on Nov. 27, 2003 and filed on May 23, 2002 by Datta et al.

Additional information on suitable disposable child sized implement, nonwoven sheet members and/or retaining aids may be found in copending U.S. Provisional Patent Application Nos. 60/453,160 filed on Mar. 10, 2003, entitled "Disposable Nonwoven Cleansing Mitt" in the name of Dobrin et al; 60/453,166 filed on Mar. 10, 2003, entitled "Disposable Nonwoven Cleansing Mitt" in the name of Benjamin et al; and 60/453,167 filed on Mar. 10, 2003, entitled "Child's Cleansing System" in the name of Sanchez et al.

The manufacture of disposable cleaning implements, mitts, nonwoven sheet member and components thereof, such as, nonwoven sheet substrate per se forms no part of this invention.

Personal Care Compositions

The personal care compositions releasably carried by the disposable cleaning implement of the present invention may comprise a variety of components such as are conventionally used in personal care compositions. These optional components should be suitable for application to a child's skin and hair; that is, when incorporated into the implement they are suitable for use in contact with human skin without undue toxicity, incompatibility, irritation, instability, allergic response, and the like, within the scope of sound medical or formulator's judgment.

In one embodiment of the present invention the personal care compositions are in the form of a paste, or a dry solid. While personal care compositions comprising more than about 50% by weight of the composition of a liquid carrier, such as water, are within the scope of the present invention, it is preferred that any disposable cleaning implement be mostly dry, more preferably dry to the touch, prior to contact with the washing environment, that is, until the child first immerses the disposable cleaning implement or otherwise contacts it with water. Typically, this translates into levels of liquid carrier, such as water, of less than or equal to about 10%, more preferably less than or equal to about 7% by weight of personal care composition.

In one alternative embodiment of the present invention the amount of personal care composition present in the disposable cleaning implement is preferably present in amounts from about 1 gsm to about 200 gsm, more preferably from about 10 gsm to about 175 gsm, even more preferably still from about 20 gsm to about 150 gsm. (Grams of personal care composition per square meter of nonwoven sheet member) Alternatively, each disposable cleaning implement may contain from about 1 g to about 20 g, more preferably from about 1 g to about 15 g of personal care composition per disposable cleaning implement.

Aromatherapy Adjuvant

Aromatherapy has been used for centuries as a way to promote physical and mental well being. Essential oils extracted from flowers, fruit, seeds, nuts, herbs, spices, woods, bark, roots, fibers and the like, when inhaled, are believed to have subtle effects on a person's mind and emotions. In addition, while not wishing to be limited by theory, it is believed that when the essential oils penetrate the skin and enter the bloodstream and immune system, they work in a physiological manner to promote healing.

Essential oils are highly scented droplets found in minute quantities in the flowers, stems, leaves, roots and barks of aromatic plants. They are highly fluid and exceptionally volatile and potent.

Essential oils are complex mixtures of different organic molecules, such as terpenes, alcohols, esters, aldehydes, ketones and phenols. While not wishing to be limited by theory, it is believed that it is the interaction between each and every component and/or molecule that gives an essential oil its particular character and unique therapeutic properties. Furthermore, while not wishing to be limited by theory it is also believed that the use of one or more aromatherapy adjuvants in the present personal care composition not only provides a calming effect to a child, it may also provide beneficial healing effects.

Typically, the aromatherapy adjuvant may be any suitable compound or mixture of compounds which is detectible or perceivable by a human nose. In one preferred embodiment the aromatherapy adjuvant is an essential oil extracted from flowers, fruit, seeds, nuts, herbs, spices, woods, bark, roots, fibers and the like. Suitable essential oils for use in the present personal care composition include, but are not limited to, *Abies Sibirica* Oil, *Amyris Balsamifera* Oil, Anise (*Illicium Verum*) Oil, Balm Mint (*Melissa Officinalis*) Oil, Basil (*Ocimum Basilicum*) Oil, Bay (*Pimenta Acris*) Oil, Bee Balm (*Monarda Didyma*) Oil, Bergamot (*Citrus Aurantium Bergamia*) Oil, Birch (*Betula Aba*) Oil, Bitter Almond Oil, Bitter Orange (*Citrus Aurantium Amara*) Oil, Cabbage Rose (*Rosa Centifolia*) Oil, *Calendula Officinalis* Oil, California Nutmeg (*Torreya Californica*) Oil, *Camellia Sinensis* Oil, *Capsicum Frutescers Oleoresin*, Caraway (*Carum Carvi*) Oil, Cardamon (*Elettaria Cardamomum*) Oil, Cedarwood (*Cedrus Atlantica*) Oil, *Chamaecyparis Obtusa* Oil, Chamomile (*Anthemis Nobilis*) Oil, Cinnamon (*Cinnamomum Cassia*) Oil, Citronella (*Cymbopogon Nardus*) Oil, Clary (*Salvia Sclarea*) Oil, Clove (*Eugenia Caryophyllus*) Oil, Cloveleaf (*Eugenia Caryophyllus*) Oil, Coriander (*Coriandrum Sativum*) Oil, Coriander (*Coriandrum Sativum*) Seed Oil, *Cyperus Esculentus* Oil, Cypress (*Cupressus Sempervirens*) Oil, *Eucalyptus Citriodora* Oil, *Eucalyptus Globulus* Oil, Fennel (*Foeniculum Vulgare*) Oil, Gardenia Florida Oil, *Geranium Maculatum* Oil, Ginger (*Zingiber Officinale*) Oil, Gold of Pleasure (*Camelina Sativa*) Oil, Grapefruit (*Citrus Grandis*) Oil, Hops (*Humulus Lupulus*) Oil, *Hypericum Perforatum* Oil, *Hyptis Suaveolens* Oil, Indigo Bush (*Dalea Spinosa*) Oil, Jasmine (*Jasminum Officinale*) Oil, *Juniperus Communis* Oil, *Juniperus Virginiana* Oil, Kiwi Oil, Labdanum (*Cistus Labdaniferus*) Oil, Laurel (*Laurus Nobilis*) Oil, Lavandin (*Lavandula Hybrida*) Oil, Lavender (*Lavandula Angustifolia*) Oil, Lemon (*Citrus Medica Limonum*) Oil, Lemongrass (*Cymbopogon Schoenanthus*) Oil, *Leptospermum Scoparium* Oil, Lime (*Citrus Aurantifolia*) Oil, Linden (*Tilia Cordata*) Oil, *Litsea Cubeba* Oil, Lovage (*Levisticum Officinale*) Oil, Mandarin Orange (*Citrus Nobilis*) Oil, Massoy Bark Oil, Matricaria (*Chamomilla Recutita*) Oil, *Moroccan Chamomile* Oil, Musk Rose (*Rosa Moschata*) Oil, Myrrh (*Commiphora Myrrha*) Oil, Myrtle (*Myrtus Communis*) Oil, Norway Spruce (*Picea Excelsa*) Oil, Nutmeg (*Myristica Fragrans*) Oil, *Olax Dissitiflora* Oil, Olibanum, Opoponax Oil, Orange (*Citrus Aurantium Dulcis*) Flower Oil, Orange (*Citrus Aurantium Dulcis*) Oil, Palmarosa (*Cymbopogon Martini*) Oil, Parsley (*Carum Petroselinum*) Seed Oil, Passionflower (*Passiflora Incarnata*) Oil, Patchouli (*Pogcstemon Cablin*) Oil, *Pelargonium Graveolens* Oil, Pennyroyal (*Mentha Pulegium*) Oil, Peppermint (*Mentha Piperita*) Oil, Pine (*Pinus Palustris*) Oil, Pine (*Pinus Palustris*) Tar Oil, Pine (*Pinus Pinea*) Kernel Oil, Pine (*Pinus Pumiho*) Oil, Pine (*Pinus Sylvestris*) Cone Oil, Rosemary (*Rosmarinus Officinalis*) Oil, Rose Oil, Rose Hips Oil, Rosewood (*Aniba Rosseodora*) Oil, Rue (*Ruts Graveolens*) Oil, Sage (*Salvia Officinalis*) Oil, *Sambucus Nigra* Oil, Sandalwood (*Santalum Album*) Oil, Sandarac (*Callitris Quadrivalvis*) Gum, *Sassafras Officinale* Oil, Silver Fir Oil, *Sisymbrium Ino* Oil, Spearmint (*Mentha Viridis*) Oil, Sweet Marjoram (*Origanum Majorana*) Oil, Sweet Violet (*Viola Odorata*) Oil, Tar Oil, *Thuja Occidentalis* Oil, Tea Tree Oil, Thyme (*Thymus Vulgaris*) Oil, *Vetiveria Zizanoides* Oil, Wild Mint (*Mentha Arvensis*) Oil, *Ximenia Americana* Oil, Yarrow (*Achillea Millefolium*) Oil, Ylang Yang (*Cananga Odorata*) Oil, or any combinations thereof.

In one optional embodiment the aromatherapy adjuvant is selected from the group consisting of Anise Oil, Balm Mint Oil, Cedarwood Oil, Chamomile Oil, Citronella Oil, Clove Oil, Cloveleaf Oil, Coriander Oil, *Eucalyptus Citriodora* Oil, *Eucalyptus Globulus* Oil, Fennel Oil, Gold of Pleasure Oil, Hops Oil, Jasmine Oil, Laurel Oil, Lavandin Oil, Lavender Oil, *Moroccan Chamomile* Oil, Musk Rose Oil, Myrrh Oil, Myrtle Oil, Norway Spruce Oil, Pine Oil, Pine Tar Oil, Rosemary Oil, Rose Oil, Rosewood Oil, Sandalwood Oil, Thyme Oil, and combinations thereof.

A variety of aromatherapy adjuvants may be used in the personal care compositions of the present invention present invention. The selection of the aromatherapy adjuvant will depend upon many factors such as but not limited to, the personal care compositions (e.g., is it a body wash, shampoo, conditioner, etc.), the substrate, the user (e.g., child, caregiver, etc.) and the like.

The aromatherapy adjuvant is typically employed in personal care compositions at levels of preferably from about 0.00001% to about 10%, more preferably from about 0.00005% to about 5%, and more preferably from about 0.0001% to about 1%, by weight of the personal care composition.

Additional Odor Component:

In addition to the aromatherapy adjuvant the personal care composition may optionally contain an additional odoriferous component. These odoriferous components include but are not limited to benzenoid materials, alcohol materials, ester materials, aldehyde materials, ketone materials, and mixtures thereof. The benzenoid materials are selected from benzyl benzoate, benzyl carbinol, benzyl salicylate, benzyl cinnamate, diethyl phthalate, phenoxy ethanol, hexahydro-4,6,6,7,8,8-hexamethylcyclopenta-γ-2-benzopyran, 7-acetyl-1,1,3,4,4,6-hexamethyltetralin, 3-(3,4-methylene dioxyphenol)-2-methyl propanol, methyl-iso-eugenol, eugenol, and mixtures thereof. The alcohol materials are selected from citronellol, alcohol C-8, alcohol C-10; alcohol C-11, alcohol C-12, dipropylene glycol, linalool, geraniol, benzyl alcohol, 2-ethyl-4-(2,2,3-trimethyl-3-cyclopentene-1-yl)-2-buten-1-ol, dihydromyrcenol, and mixtures thereof. The aldehyde materials are selected from 4-(4-hydroxy-4-methylpentyl)-3-cyclohexene 1-carboxoaldehyde, p-t-butyl-α-methyldihydrocinnamic aldehyde, aldehyde C-10, aldehyde C-11, aldehyde C-12, laurinal, heliotropine, anisic aldehyde, benzyl aldehyde, and mixtures thereof. The esters materials are selected from benzyl acetate, dimethyl benzyl carbinyl acetate, ethylene brassylate, cyclopentadecanolide, linalyl acetate, benzyl proprionate, citronellyl acetate, hexyl butyrate, neryl acetate, prenyl acetate, hexyl cinnamate, oxacyclohexadecen-2-one, and mixtures thereof. The ketones materials are selected from methyl ionone, ambretone, methyl dihydro jasmonate, muscone, allyl ionone, and mixtures thereof.

The additional odoriferous component, when present is typically employed in personal care compositions at levels of preferably from about 0.00001% to about 10%, more preferably from about 0.00005% to about 5%, and more preferably from about 0.0001% to about 1%, by weight of the personal care composition.

Surfactants

The personal care compositions used in the present invention may optionally contain one or more surfactant. Typically the optional surfactant, when present, is selected from the group consisting of anionic surfactants, amphoteric surfactants, nonionic surfactants, zwitterionic surfactants, cationic surfactants, and mixtures thereof.

The surfactants of the personal care compositions may be lathering or non-lathering surfactants. As used herein, "lathering surfactant" means a surfactant, which when combined with water and mechanically agitated generates a foam or lather. A "nonlathering surfactant" produces no such foam or lather under similar conditions. It is preferred, however, that the surfactants be lathering since increased lather is important to consumers as an indication of cleansing effectiveness.

Nonlimiting examples of surfactants useful in the compositions of the present invention are disclosed in McCutcheon's, *Detergents and Emulsifiers*, North American edition (1986), published by Allured Publishing Corporation; McCutcheon's, *Functional Materials*, North American Edition (1992); and U.S. Pat. No. 3,929,678, to Laughlin et al., issued Dec. 30, 1975.

Some nonlimiting examples of suitable surfactants include ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium monolauryl phosphate, sodium cocoglyceryl ether sulfonate, sodium $C_9$-$C_{22}$ soap, amine oxides such as lauramine oxide and cocoamine oxide, decyl polyglucose, lauryl polyglucose, sucrose cocoate, $C_{12-14}$ glucosamides, sucrose laurate, fatty amines, di-fatty quaternary amines, tri-fatty quaternary amines, imidazolinium quaternary amines, PEG 80 Sorbitan laurate, PEG-150 distearate, sodium laureth-13 carboxylate, disodium lauroamphodiacetate, sodium lauroamphoacetate, cetyl dimethyl betaine, cocoamidopropyl betaine, cocoamidopropyl hydroxy sultaine, and combinations thereof.

Surfactant, when present, is typically employed in compositions at levels of preferably from about 0.01% to about 99%, more preferably from about 0.5% to about 97%, and more preferably from about 1.0% to about 98%, by weight of the personal care composition.

Adjunct Ingredients

The personal care compositions used in the present invention may optionally contain one or more adjunct ingredients. Illustrative, but nonlimiting examples of suitable adjunct ingredients include: enzymes, absorbents, aesthetic components, fragrances, pigments, colorings, colorants, skin sensates, anti-acne agents (e.g., resorcinol, sulfur, salicylic acid, erythromycin, zinc, etc.), anti-caking agents, antifoaming agents, preservative, conditioners, hair conditioners, dye, antimicrobial agents (e.g., quaternium-15, paraben preservatives such as, but not limited to, ethyl paraben, DMDM hydantoin, iodopropyl butylcarbamate(IPBC), etc.), glycerin, binders, buffering agents, bulking agents, chelating agents (e.g., EDTA, etc.), solvents, cosmetic biocides, denaturants, external analgesics, film formers or materials, e.g., polymers, for aiding the film-forming properties and substantivity of the composition (e.g., copolymer of eicosene and vinyl pyrrolidone), humectants, polydimethylsiloxanes (such as, but not limited to, dimethicones), Cyclic polyalkylsiloxanes, opacifying agents, pH adjusters, process aids, reducing agents, sequestrants, skin-conditioning agents, moisturizers, skin soothing and/or healing agents (e.g., panthenol and derivatives (e.g., ethyl panthenol), flavonoids (e.g., bioflavonoids, flavones, isoflavones, etc.), conditioners (e.g., hair conditioners), aloe vera, pantothenic acid and its derivatives, allantoin, bisabolol, and dipotassium glycyrrhizinate), hair detanglers, skin treating agents, thickeners (e.g., polymeric thickeners, gums, etc.), hydrocolloids, zeolites, sugar amines also known as Amino sugars (e.g., glucosamine, N-acetyl glucosamine, mannosamine, N-acetyl mannosamine, galactosamine, N-acetyl galactosamine, their isomers (e.g., stereoisomers), and their salts (e.g., HCl salt)), phytosterols (e.g., β-sitosterol, campesterol, and the like), oxidants/radical scavengers (such as ascorbic acid (vitamin C), ascorbyl esters of fatty acids, ascorbic acid derivatives (e.g., magnesium ascorbyl phosphate), tea extracts (such as green tea extracts), plant and fruit extracts (e.g., grape skin/seed extracts, melanin, and rosemary extracts, Manjistha, Guggal, kola extract, chamomile, red clover extract, sea whip extract), caffeine, candelilla wax, alpha-bisabolol, aloe vera, allantoin, glycyrrhetic acid, glycyrrhizic acid, abrasives, astringents, etc. (e.g., menthol, menthyl lactate, etc.), binders, gelling agents, thixatropic agents, bulking agents, cosmetic astringents, cosmetic biocides, denaturants, opacifying agents, pH adjusters, reducing agents, sequestrants, skin bleaching and lightening agents (e.g., hydroquinone), skin treating agents, sunscreen actives (e.g., p-aminobenzoic acid, 2-ethylhexyl-p-methoxycinnamate, 2,2'-dihydroxy-4,4'-dimethoxybenzophenone, zinc oxide, titanium dioxide etc,), and vitamins and derivatives thereof (e.g., tocopherol, tocopherol acetate, beta carotene, nicotinic acid, retinoic acid, retinol, retinoids, retinyl palmitate, niacin, pantothenic, niacinamide, nicotinyl alcohol, and the like). The personal care compositions releasably contained by the disposable implement may include carrier components such as are known in the art, for example, water, alcohols, polyols, and the like. Such carriers can include one or more compatible liquid or solid filler diluents or vehicles which are suitable for application on to and/or use by a child. Alternatively these carriers may be present in the personal care composition during formulation and application to the implement and subsequently removed, by any conventional means, such as, but not limited to, heating, reducing air pressure, and the like.

Additional information on suitable personal care compositions, surfactants and other possible components thereof may be found in: CTFA Cosmetic Ingredient Handbook, Second Edition (1992); CTFA International Cosmetic Ingredient Dictionary, Fifth Edition, 1993; McCutcheon's, Detergents and Emulsifiers, North American edition (1986), published by Allured Publishing Corporation; McCutcheons, Functional Materials, North American Edition (1992); Sagarin, et al., Cosmetics Science and Technology (1972); U.S. Pat. No. 3,929,678, to Laughlin et al., issued Dec. 30, 1975; U.S. Pat. No. 5,833,998 issued to Biedermann et al., on Nov. 10, 1998; U.S. Pat. No. 5,939,082 issued to Oblong et al., on Aug. 17, 1999; U.S. Pat. No. 3,755,560, issued Aug. 28, 1973, to Dickert et al.; U.S. Pat. No. 4,421,769, issued Dec. 20, 1983, to Dixon et al.; U.S. Pat. No. 4,960,764, to Figueroa, Jr. et al., issued Oct. 2, 1990; U.S. Pat. No. 6,335,312 issued on Jan. 1, 2002 to Coffindaffer et al.; U.S. Pat. No. 5,607,980, issued to McAtee et al., on Mar. 4, 1997; U.S. Pat. No. 5,487,884, issued Jan. 30, 1996 to Bissett et al.; U.S. Pat. No. 5,686,082, issued to N'Guyen on Nov. 1, 1997; U.S. Pat. No. 2,831,854, issued to Tucker et al., on Apr. 22, 1958; U.S. Pat. No. 4,005,196, to Jandacek, issued Jan. 25, 1977; U.S. Pat. No. 4,005,195, to Jandacek, issued Jan. 25, 1977; U.S. Pat. No. 5,306,516, to Letton et al., issued Apr. 26, 1994; U.S. Pat. No. 5,306,515, to Letton et al., issued Apr. 26, 1994; U.S. Pat. No. 5,306,514 to Letton et al., issued Apr. 26, 1994; U.S. Pat. No. 4,797,300, to Jandacek et al., issued Jan. 10, 1989; U.S. Pat. No. 3,963,699, to Rizzi et al., issued Jun. 15, 1976; U.S. Pat. No. 4,518,772, to Volpenhein, issued May 21, 1985; U.S. Pat. No. 4,517,360, to Volpenhein, issued May 21, 1985; U.S. Pat. No. 4,976,953, to Orr et al., issued Dec. 11, 1990; U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al., issued Dec. 9, 1986; U.S. Pat. No. 4,599,379 to Flesher et al., issued Jul. 8, 1986; U.S. Pat. No. 6,200,554, issued to Yeoh et al., on Mar. 13, 2001; U.S. Pat. No. 6,248,317 issued to Snyder et al., on Jun. 19, 2001; U.S.

Pat. No. 4,741,855 issued to Grote et al., on May 3, 1988 and re issued as U.S. Pat. No. RE 34,584 on Apr. 12, 1994; U.S. Pat. No. 6,280,751 issued to Fletcher et al., on Aug. 28, 2001; U.S. Pat. No. 6,506,394 issued to Yohiaoui et al., on Jan. 14, 2003; U.S. Pat. No. 6,440,437 issued to Krzysik et al., on Aug. 27, 2002; U.S. Pat. No. 6,630,175 issued to Shapiro et al., on Oct. 7, 2003; EP 228,868, to Farrar et al., published Jul. 15, 1987; WO 97/39733 A1, published on Oct. 30, 1997; US. Patent Application No. US20030190337A1: "Methods for regulating the condition of mammalian keratinous tissue via topical application of vitamin B6 compositions", published on Oct. 9, 2003; US. Patent Application No. US20030130636A1: "System for improving skin health of absorbent article Wearers", published on Jul. 10, 2003; and US. Patent Application No. US20020177535A1: "Cleansing compositions with milk protein and aromatherapy", published on Nov. 28, 2002.

Mixtures of the above components may also be used.

Also, when applicable, the pharmaceutically-acceptable salts, of the components are useful herein.

Adjunct ingredients, when present, are each typically employed in compositions at levels of from about 0.0001% to about 99.9%, preferably from about 0.001% to about 99%, and more preferably from about 0.01% to about 97%, by weight of the personal care composition.

In preparing the disposable cleaning implement of the present invention the personal care composition need to be releasably carried by the disposable cleaning implement, such as placed on one of the nonwoven sheet members. Techniques for combining the disposable cleaning implement or nonwoven sheet members with the personal care composition are well known in the art. Examples of common methods of combining the personal care composition with the disposable cleaning implement may involve coating, immersing, dipping, printing, and/or spraying, a nonwoven sheet member with the personal care composition. The personal care composition of is added to the disposable cleaning implement at level sufficient to provide the desired benefits of the present invention. One illustrative convenient method of combining the personal care composition of the present invention with the disposable cleaning implement is for the personal care composition to be applied to a nonwoven sheet member while the nonwoven sheet member is a continuous web. The application could be in many forms, including one or more of, but not limited to coating, immersing, dipping, spraying, printing, extruding and the like. Once the personal care composition is applied the nonwoven sheet member is cut to the desired length to form the disposable cleaning implement and then packaged for sale. Alternatively, the personal care composition may be added to a nonwoven sheet member when the nonwoven sheet member is part of a formed mitt.

The personal care composition may be added to the disposable cleaning implement in any convenient fashion. For example, the personal care composition components could all be mixed together and then sprayed onto a nonwoven sheet member; each component could be deposited on a nonwoven sheet member separately; or half the components could be mixed together and then added to a nonwoven sheet member, with the remainder then being mixed together and then sprayed on to a nonwoven sheet member.

In one optional embodiment of the present invention the personal care composition is applied to the implement, in the form of a paste prior to the assembly of the disposable cleaning implement. This optional embodiment is more preferably a "hot melt" composition. Hot melt composition have high viscosity at or around room temperature, and then melt (become substantially liquid) at higher temperatures. Such systems are advantageous during processing of a disposable, substantially dry (or dry to the touch) child's cleansing mitt since the composition can be applied (e.g., coated, sprayed, extruded) to the implement at a low viscosity (e.g., a liquid) at higher than room temperature, and then as the composition cools down, it becomes a high viscosity paste or solid.

Once the personal care composition is applied to the disposable cleaning implement or components thereof, such as but not limited nonwoven sheet members, it may be further treated in any conventional manner, such as but not limited to, heating to remove excess water from the personal care composition.

Child Graphic

The child graphic may be any suitable visual image or images. The child graphic may include pictorial symbols and/or images, such as but not limited to, photographs, such as but not limited to: a photograph of a child using the disposable child sized implement; drawings, such as a drawing of a child or an anthropomorphic image of an animal or object (See FIGS. 4-24) using the disposable child sized implement; cartoons, such as but not limited to, well known cartoon characters, well known brand logos or the like, or characters specifically created to be associated with the implement of commerce; symbols, such as but not limited to arrows, indications or motion or movement, and the like; and combinations thereof.

Figure 4:
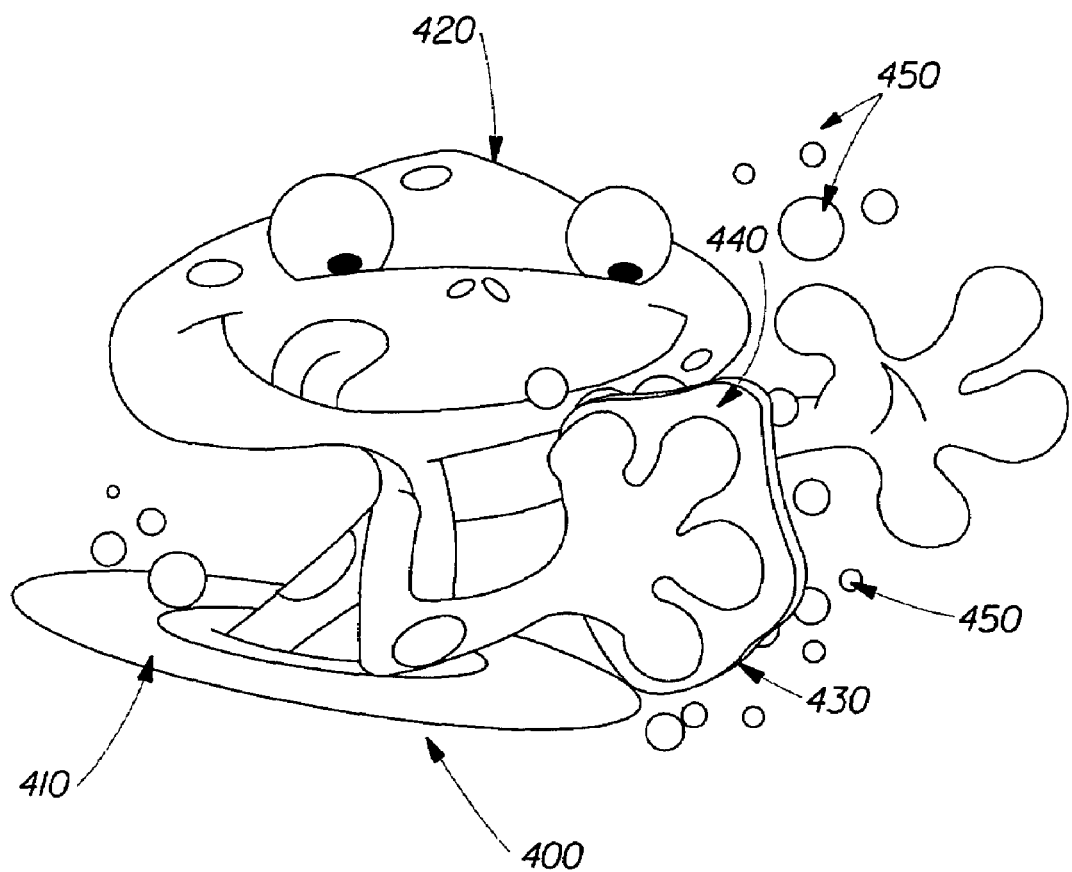
FIG. 4 illustrates a child graphic.

The child graphic may be arranged in any suitable fashion and may be in the form of one or more pictorial images. The arrangement may include the child graphic in, for example, a single image or picture, such as in a single image or a single cartoon. FIG. 4 illustrates a single image 400 which includes a child graphic. The child graphics present in image 400 include an anthropomorphic animal 420, in this case a frog, who is in a body of water 410, holding a disposable child sized implement 430 in his hand. It is preferred that the disposable child sized implement illustrated in the child graphic or child graphics be similar in appearance, at least to a child, to any disposable child sized implement in association with the child graphic or child graphics. The image further illustrates that frog 420, is cleaning himself thereby generating suds and bubbles 450 using the disposable child sized implement 430 by contacting parts of his body 440 with the disposable child sized implement 430.

In an optional embodiment of the present invention, the child graphic is a sequential series of panels, wherein each of the panels contains, for example, a different cartoon, symbol, drawing, photograph and combinations thereof. Alternatively, each panel may contain one or more child graphic. These panels may be arranged in any suitable fashion, such as but not limited to, vertically, horizontally, diagonally, circular, and the like and combinations thereof. Examples of this optional embodiment can be found in FIGS. 5, 7, and 8.

Figure 5:
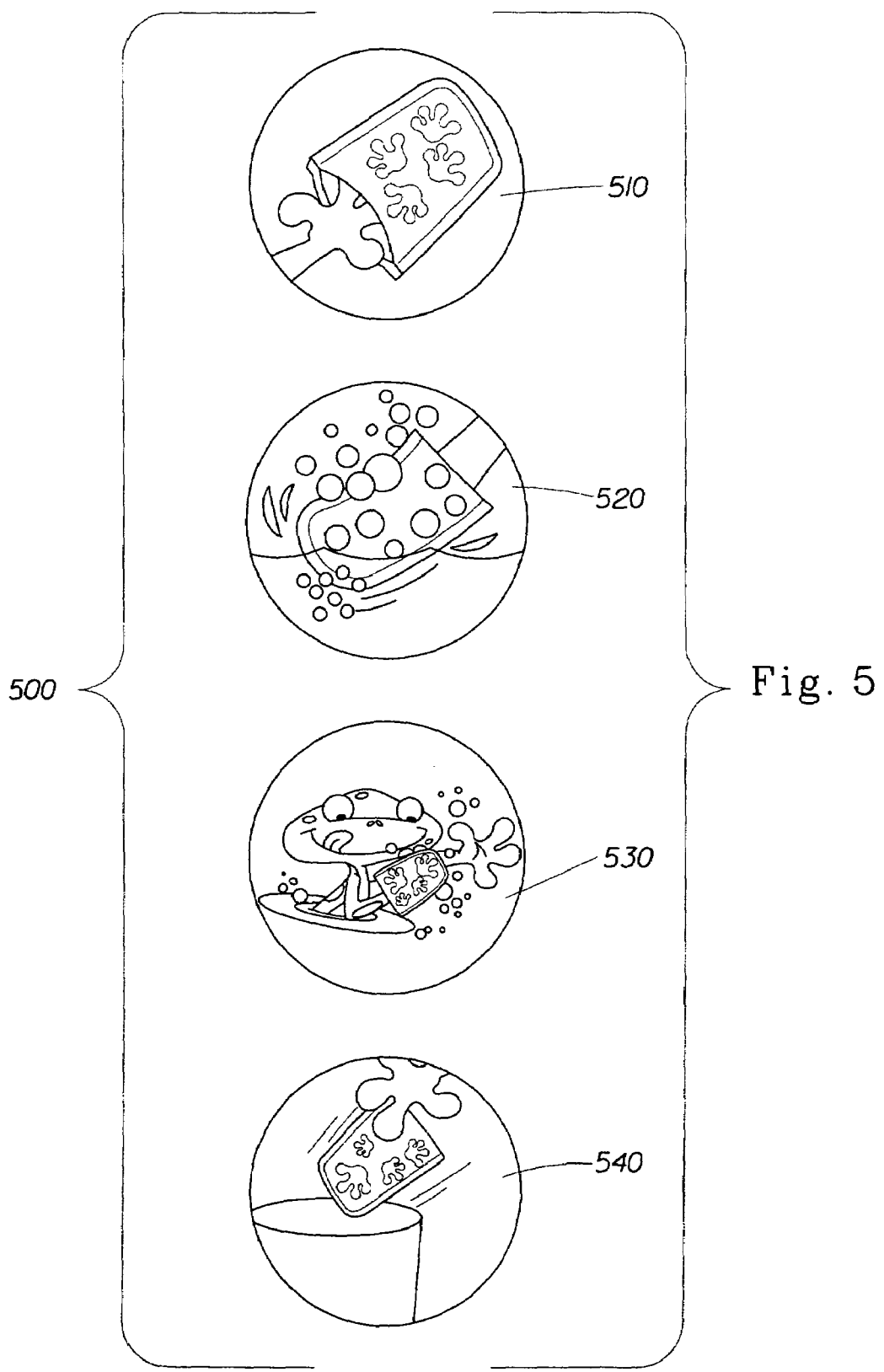
FIG. 5 Illustrates one embodiment of a disposable nonwoven child's cleansing mitt having a portion of child graphic of FIG. 4.

In FIG. 5 panels 500 are a child graphic comprising a sequential series of panels communicating to a child incapable of reading how to use a disposable child sized implement which is similar to the disposable child sized implement illustrated in FIG. 2. Panel 510 communicates where the child places its hand and the orientation of the disposable child sized implement relative to the child. Panel 520 communicates that the child needs to contact the disposable child sized implement with water, such as by immersion in a body of water such as a bath. Panel 520 also communicates to the child that the benefit composition is only present on one side of the disposable child sized implement. Additionally, panel 520 reinforces the prior communication in panel 510 on the correct orientation of the disposable child sized implement relative to the child. Panel 530, that is the frog character, additionally communicates to the child that in order to clean themselves they need to contact, such as by rubbing, scrubbing and the like, their body with the side of the disposable child sized implement which will generate lather. Additionally, panel 530 further reinforces the prior communication in panels 510 and 520 on the correct orientation of the disposable child sized implement relative to the child. Panel 540 communicates the need for the child to properly dispose of the child's cleansing mitt after they have finished bathing.

Figure 6:
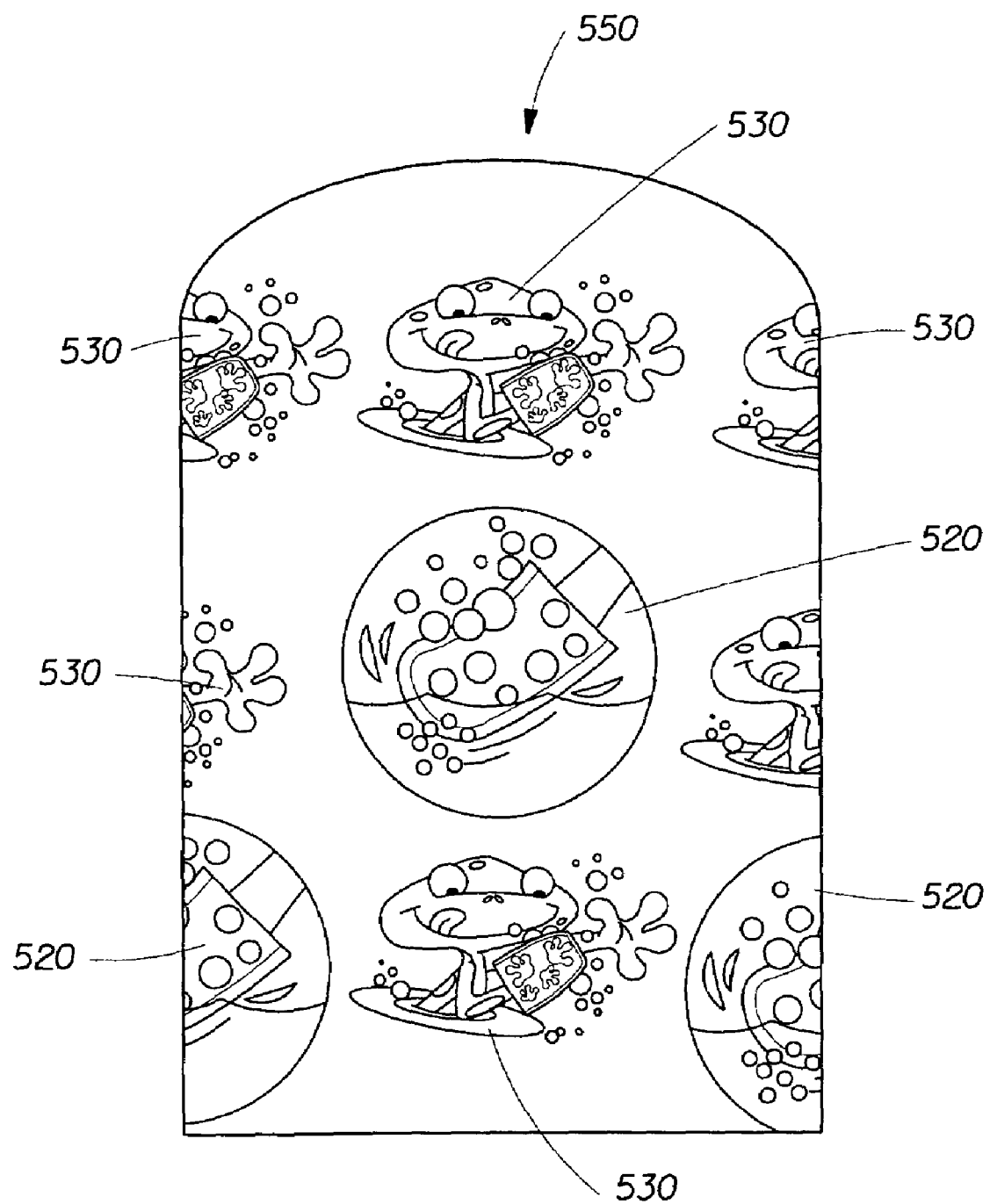
FIG. 6 illustrates another child graphic.

FIG. 6 shows a disposable child sized implement 550 containing a repeating pattern two of the child graphics of FIG. 5, namely a repeating pattern of panels 520 and 530. Disposable child sized implement 550 may be used in combination with a container which has, for example, printed thereon the entire set, or only panels 510 and 540, of FIG. 5. These panels on the disposable child sized implement 550 would provide additional reinforcement to the child as to the correct use of the disposable child sized implement 550.

Figure 7:
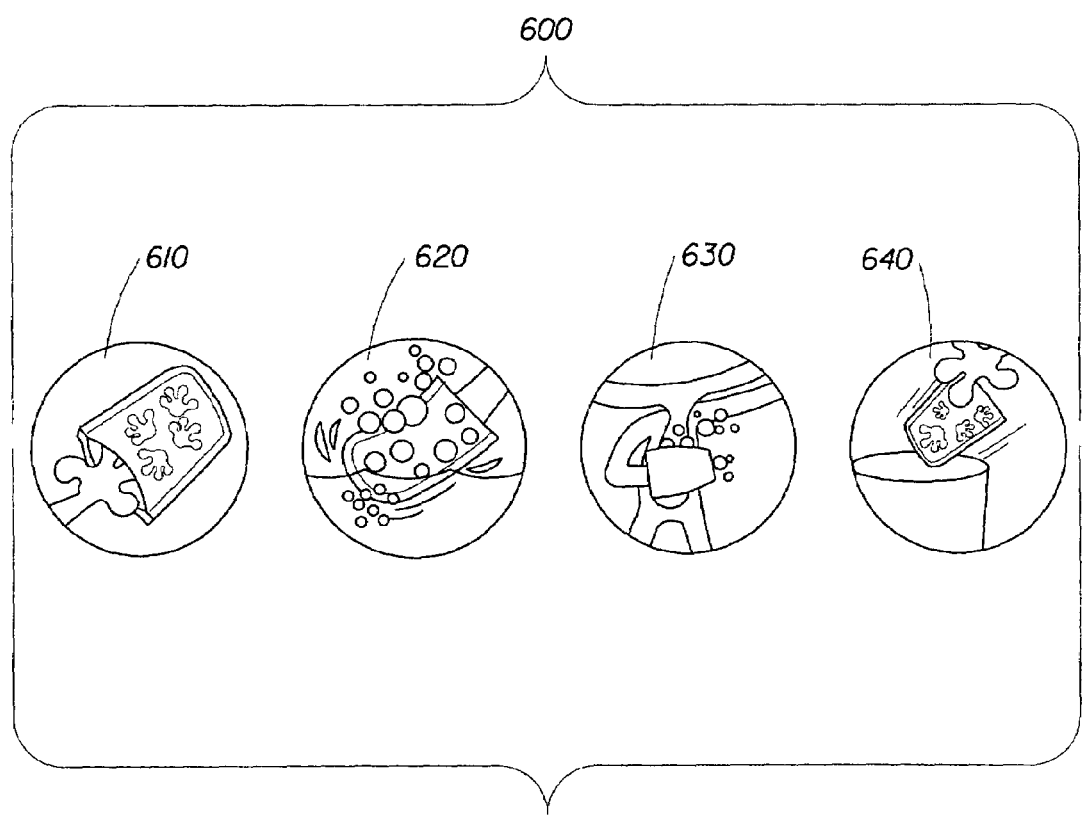
FIG. 7 illustrates another child graphic.

In FIG. 7, panels 600 are a sequential series of panels each comprising a different child graphic that are communicating, especially communicating to a child incapable of reading, how to use a disposable child sized implement which is similar to the disposable child sized implement illustrated in FIG. 2. Panel 610 communicates where the child places its hand to wear the disposable child sized implement and the correct orientation of the disposable child sized implement relative to the child. Panel 620 communicates not only that the child needs to contact the disposable child sized implement with water, such as by immersion in a body of water such as a bath, but that the benefit composition will generate lather when combined with water. Panel 620 also communicates to the child that the benefit composition is only present on one side of the disposable child sized implement. Additionally, panel 620 reinforces the prior communication in panel 610 on the correct orientation of the disposable child sized implement relative to the child. Panel 630 reinforces the information communicated in previous panels 610 and 620 by again communicating that the benefit composition will generate lather and is only present on one side of the disposable child sized implement. Panel 630 additionally communicates to the child that in order to clean themselves they need to contact, such as by rubbing, scrubbing and the like, their body with the side of the disposable child sized implement which will generate lather. The frog character in panel 630 communicates to the child that the disposable child sized implement is suitable for use while they are in a bath or similar body of water. Panel 640 communicates the need for the child to properly dispose of the disposable child sized implement after they have finished bathing.

Figure 8:
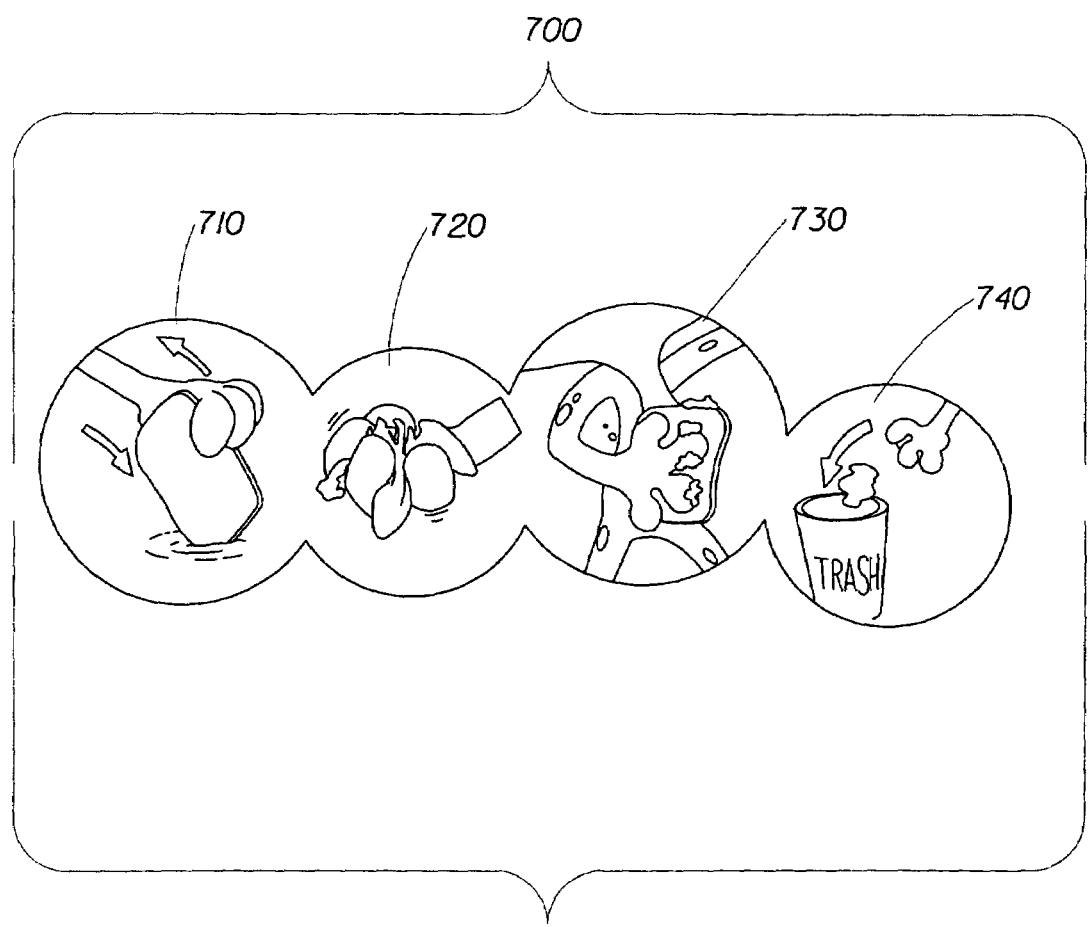
FIG. 8 illustrates another child graphic.

In FIG. 8, panels 700 are a sequential series of panels each comprising a different child graphic communicating to a child incapable of reading how to use a disposable cleaning implement. Panel 710 visually communicates that the child needs to contact the disposable cleaning implement with water, such as, by immersion in a body of water such as a bath. Panel 710 also visually communicates through arrows how a child immerses the disposable cleaning implement. Panel 720 visually communicates that the personal care composition will generate lather. Furthermore, panel 720 visually communicates through the use of a hand and motion lines, that the child needs to squeeze or exert some compressive force on the disposable cleaning implement after contact it with water to generate foam. The frog cartoon character in panel 730 communicates to the child that in order to clean themselves they need to contact, such as by rubbing, scrubbing and the like, their body with the disposable cleaning implement. Panel 730 further communicates to the child that the disposable cleaning implement is suitable for use on the child's entire body. Panel 740 communicates the need for the child to properly dispose of the disposable cleaning implement after they have finished bathing.

Figure 23:
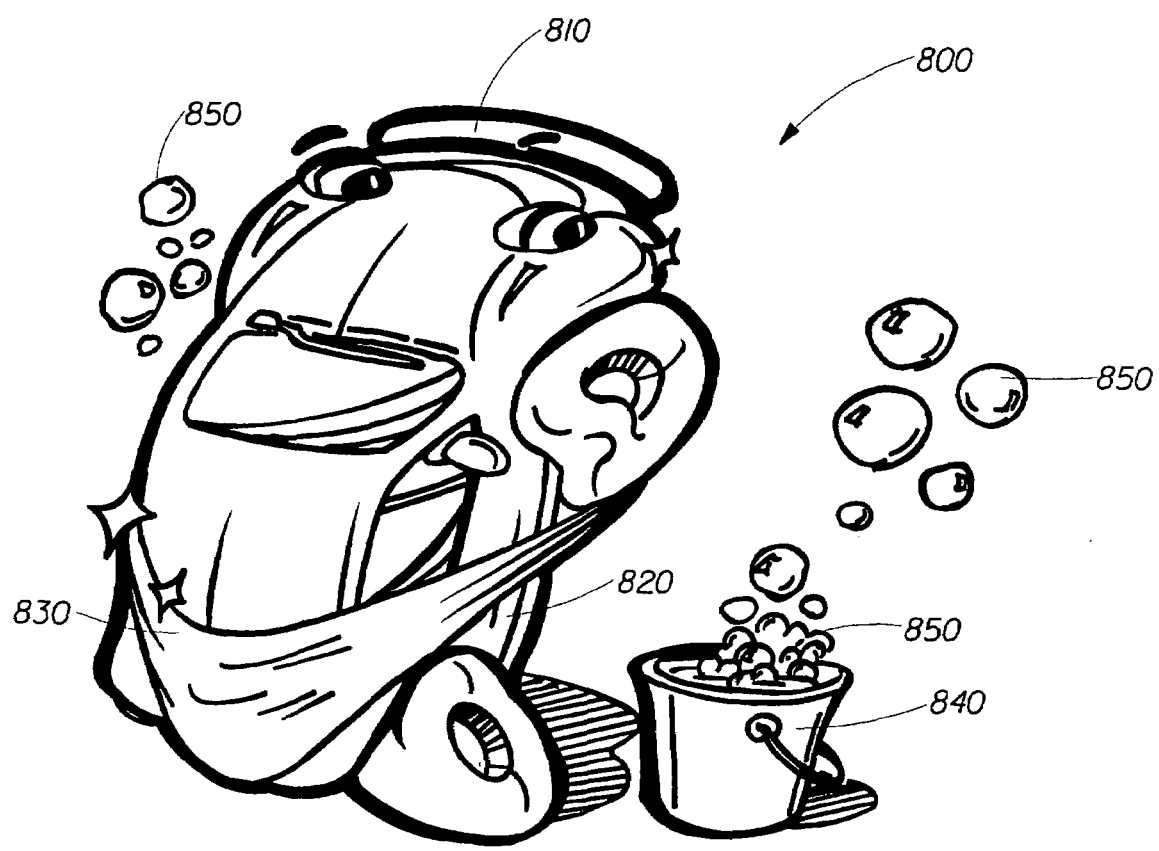
FIG. 23 illustrates another child graphic.

FIG. 23 illustrates an image 800 which includes a child graphic 810. The child graphic 810 present in image 800 includes a character graphic, specifically an anthropomorphic object 820, in this case an automobile, who is standing and drying itself with a towel 830. The image 800 further includes a bucket 840 which is full of a liquid which is generating bubbles 850.

FIGS. 9 to 24 illustrate additional exemplary child graphics, depicting a character, in these figures frogs, monkeys, turtle or automobile in a range of various activities that a child may typically be engaged in or would readily be able to imaging themselves in that action or activity, either in place of the character or doing the activity along with the character.

Figure 9:
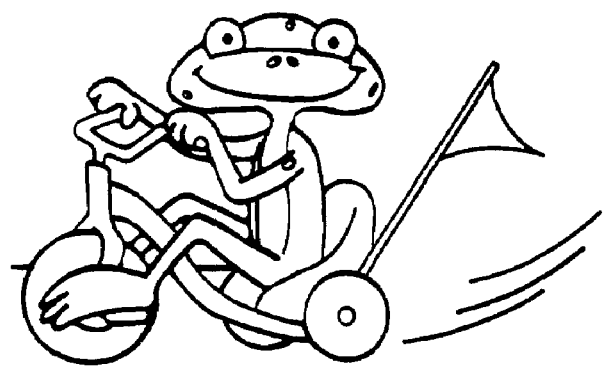
FIG. 9 illustrates another child graphic.
Figure 10:
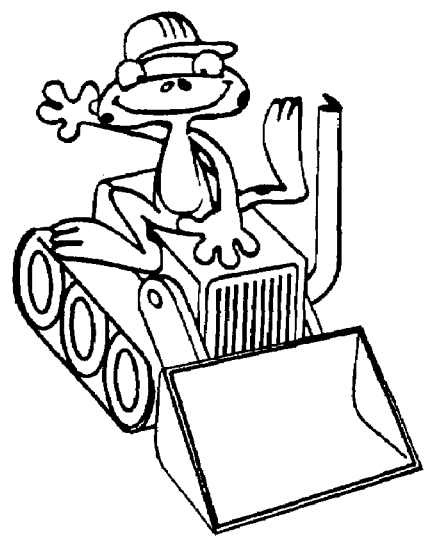
FIG. 10 illustrates another child graphic.
Figure 11:
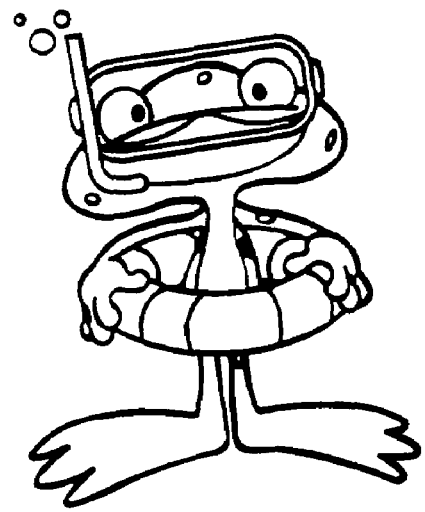
FIG. 11 illustrates another child graphic.
Figure 12:
FIG. 12 illustrates another child graphic.
Figure 13:
FIG. 13 illustrates another child graphic.
Figure 14:
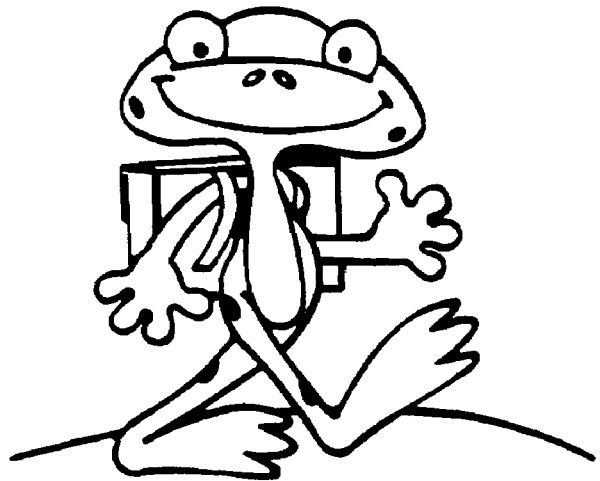
FIG. 14 illustrates another child graphic.
Figure 15:
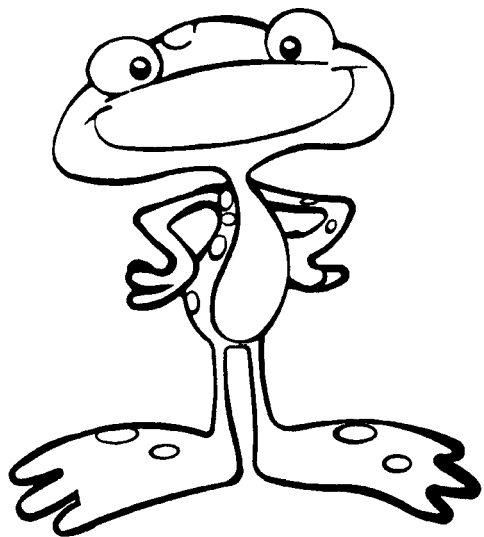
FIG. 15 illustrates another child graphic.
Figure 16:
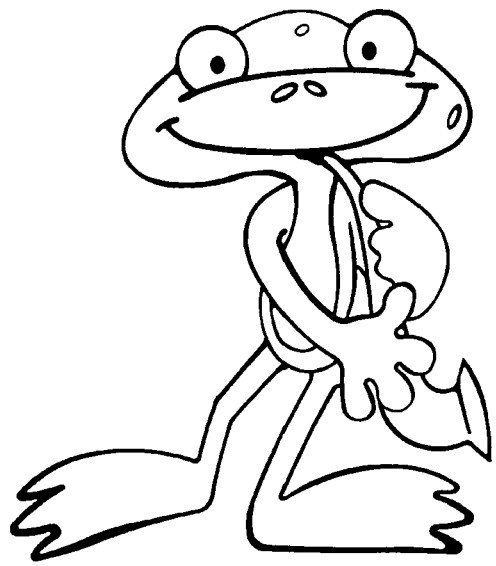
FIG. 16 illustrates another child graphic.
Figure 17:
FIG. 17 illustrates another child graphic.
Figure 18:
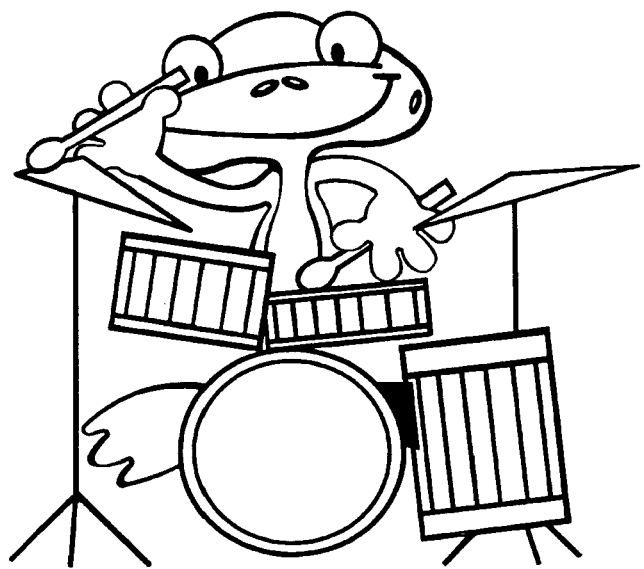
FIG. 18 illustrates another child graphic.
Figure 19:
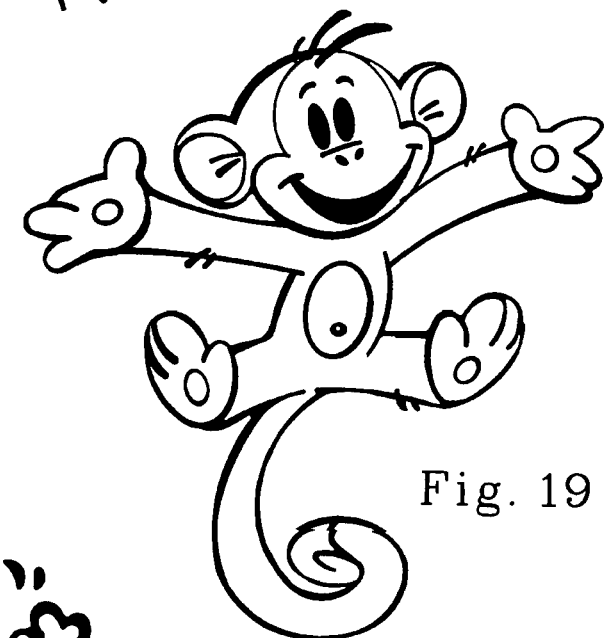
FIG. 19 illustrates another child graphic.
Figure 20:
FIG. 20 illustrates another child graphic.

The child graphic or child graphics may also include a story line in which a character, such as the as the frogs, monkeys, turtle and automobile of FIGS. 9 to 24, is illustrated performing an activity which will preferably lead to the character needing to perform an activity which may involve the use of the disposable child sized implement. Illustrative, but non limiting examples of such activities include, running, riding (for example riding a tricycle as illustrated in FIG. 9 or a bulldozer as illustrated in FIG. 10), playing in the mud, playing with a ball (FIG. 12), playing hide and seek, or other similar activities which a child does and can relate to. In this way, the child graphic or child graphics may permit the caregiver to interact with the child regarding the story line created by the child graphic or child graphics and may provide an opportunity for the caregiver to teach the child important life lessons, such as bathing and cleaning, due to the interactive nature of the child graphic.

In one alternative embodiment of the present invention when the disposable implement comprises two or more child graphics, and/or the disposable implement is present in a container which has one or more child graphics, these different child graphics may be have a common storyline.

In one alternative embodiment of the present invention when the disposable implement comprises two or more child graphics, and/or the disposable implement is present in a container which has one or more child graphics, these different child graphics may be have a related in subject matter.

Figure 24:
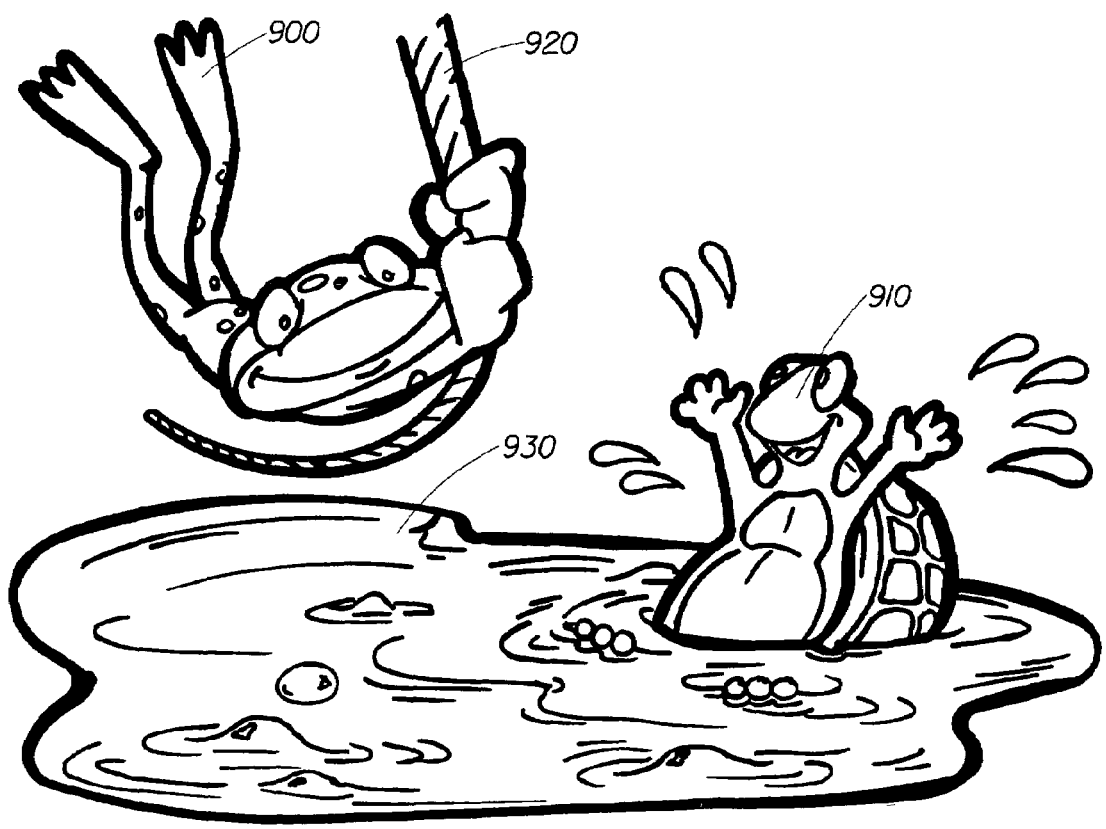
FIG. 24 illustrates another child graphic.

FIG. 24 illustrates a pair of child graphics, in this case two character graphics, a frog 900 and a turtle 910 which have a common story line and are related in subject matter. The frog 900 is swinging on a rope 920 over a pool or pond 930 in which the turtle 910 is frolicking and splashing.

In one alternative embodiment of the present invention when the disposable implement comprises two or more child graphics, and/or the disposable implement is present in a container which has one or more child graphics, these different child graphics may be unrelated in subject matter.

The child graphic may optionally include a character graphic that can increase the child's interest in using the disposable child sized implement and can increase the opportunities for the caregiver to interact positively with the child. The term "character graphic" is used herein to refer to a child graphic containing an anthropomorphous image, and in particular an image having or suggesting human form or appearance which ascribes human motivations, characteristics or behavior to inanimate objects, animals, natural phenomena, toys, cartoon characters, or the like. Ideally the character graphic would be suitable for children's swimwear, toys, clothing, diapers or the like and could be utilized to motivate children to use the disposable child sized implement. To that end, the character graphics can be associated with popular characters in the media, advertising or well known in a particular culture. Ideally they are characters that the child or caregiver care about and want to identify with. Ideally the child can imagine himself or herself taking the place of the character or emulate the character's behavior/attitude.

The role of the character graphic in the child graphic can be to encourage a child and to motivate them to behaviors, such as but not limited to, cleaning themselves, cleaning their room, and the like. The character graphic may provide a source of entertainment and reassurance for the child and a buddy, or friend, who reduces stress and can be related to in a non-competitive fashion during the training period. The character may also provide positive reinforcement and encouragement to the child while the child is learning new skills and behaviors in a non-competitive or threatening manner.

Suitable character graphics can include animals, people, inanimate objects, natural phenomena, cartoon characters or the like, that can or can not be provided with human features such as arms, legs, facial features or the like. It may be desirable for the character graphic to be familiar to the child, such as an identifiable cartoon character. The character graphics should at least be a type that the child can relate to, examples of which could include animals, toys, licensed characters, or the like. Character graphics can be made more personable and friendly to the child by including human-like features, human-like expressions, apparel, abilities, or the like. In one optional embodiment it is desirable for a character to have a distinguishing feature or features, which in a pictograph can help in training, such as a frog's webbed hand. By way of illustration, an animal character graphic can be shown smiling, wearing clothing, playing sports, fishing, driving, playing with toys, or the like. In particular embodiments, the character graphic can desirably be created to project an appearance that could be described as friendly, positive, non-intimidating, silly, independent, inspirational, active, expressive, dauntless and/or persevering. For example, the frog 420 of FIG. 4 is one example of such a character graphic and is intended to inspire the child to learn how to bathe and clean themselves. The frog's expression clearly shows that while he is concentrating on cleaning himself and becoming independent, he is still smiling and having fun. Additionally, it is preferred that the characters expressions are exaggerated so as to not be too subtle for a child to understand.

Furthermore the combination of story line and character graphics are believed to make children more interested in the use of the disposable child sized implement, such as but not limited to an implement for use in a bathing or cleaning process, and therefore lead to enhanced results. While not wishing to be limited by theory it is believed that the child graphic and the other elements of the disposable child sized implement work together to provide to a child, and especially those who are incapable of reading, the appropriate tools, directions in the use of those tools and positive reinforcement which enables the child to learn how to, for example clean themselves, wash their hair, clean their room, and the like.

The character graphic, or parts thereof may retain essentially the same appearance and/or shape while the child is using the disposable implement. Alternatively, the character graphic, or parts thereof may, change appearance, shape, appear and/or disappear while the child is using the disposable implement. That is a use indicator may be optionally a part of a child graphic, or a child graphic when more than one child graphic is present. This change may occur in any suitable manner or fashion, such as but not limited to exposure to a specific environment (e.g., water, air, other suitable chemicals, a pH or pH range), time, abrasion or similar physical force or contact, and the like and combinations thereof. One example of this may be a character who is gesturing hello, welcome or the like, is changed after the child has immersed the implement in water and uses the implement, to a gesture of goodbye.

In one optional embodiment the child graphic may optionally include a character graphic which is associated with a line of children's consumer products, such as but not limited to personal cleansing products and the like. The character may be one of a family, group, team, or the like, each member of which is designed to be associated with, for example, a consumer product, a cleaning event such as washing hair, an age group, stage of infant development and the like. Alternatively, all of the characters of a family, group, team, or the like, may be designed to be associated with the entire range of consumer products.

The association by the child of the character with the consumer product, cleaning event, etc., encourages and provides a way for the child to visualize through their imagination the character using the disposable child sized implement in the way intended. Furthermore, since this teaching is through the use of the child's imagination, there are none of the negative connotations associated with conventional parental instruction on how to use a consumer product, such as the disposable child sized implement. Instead of the child being subjected to parental nagging to do something the child really doesn't want to do, the child will actively use the disposable child sized implement as part of active learning play to interact with their new buddy, or friend, and imitate behavior. The interaction between the child and the character is only limited by the bounds of the child's imagination. The role of the caregiver or parent in then becomes one of actively encouraging imaginative play by the child with the character to use the disposable child sized implement correctly, instead of a being perceived by the child as a parent who stops play. Play is actively encouraged and new skills become part of play; "uninterrupted play". Since the use of the disposable child sized implement is essentially play, the child is eager to use the disposable child sized implement and learn the skill.

A family or group of character graphics can be used to progress a child through a system of consumer products, especially systems including the disposable child sized implement and the like. In this embodiment each character of the family or group, would be tailored to appeal to different groups of children. These groups may be based on age, development stages, regions, etc. Alternatively, a single character may be tailored for one particular group consumer products of line of consumer products which are different for children at different ages, development stages, etc. In this case the character may, for example be, of a different age depending on the consumer product and which group of children the product is intended to be used by.

Child graphics, such as but not limited to character graphics act to enable and encourage the desired behavior, such as the correct use of the disposable child sized implement, by providing stimuli. For example, in the case of a child graphic containing a character the stimuli may be entertainment and a friend.

Container

In one optional embodiment of the present invention the disposable child sized implement may be present in a container. The container may be any suitable container which is capable of removably holding at least one disposable child sized implement. The container may be rigid or it may be semi-rigid. Typically, any container will have a portion for storage of the disposable child sized implement. The size of the storage portion will depend upon the many factors, such as but not limited to, the size of the disposable child sized implement(s), the number of disposable child sized implements initially present in the container, ease of use by a child, etc. This storage portion may be accessed in any suitable fashion through an opening, or orifice of a size which is suitable for the size of the disposable implement.

Containers useful include but are not limited, PET tubs, flow wrap pouches, precut sachets for individually packed disposable child sized implement's, and other packaging known in the art as suitable for nonwoven implements releasably carrying a composition, such as but not limited to reach in or so called pop-up containers.

Furthermore, when present the container may be in the shape of a character, such as, but not limited to a character present in the child graphics present one or more of the disposable child sized implement.

Additional information on containers, as well as additional option components for containers, including but not limited to: container bodies; lids; containers features, such as but not limited to, attachments of lids, hinges, zippers, securing means; and the like, can be found in U.S. Pat. Nos. Des 451,279 issued on Dec. 4, 2001, to Chin; Des 437,686 issued on Feb. 20, 2001, to Balzar; Des 443,508 issued on Jun. 12, 2001, to Braaten; Des 443,451 issued on Jun. 12, 2001, to Buck; Des 421,901 issued on Mar. 28, 2000, to Hill; Des 421,902 issued on Mar. 28, 2000, to Hill; Des 416,794 issued on Nov. 23, 1999, to Cormack; Des 414,637 issued on Oct. 5, 1999, to Amundson; Des 445,329 issued on Jul. 24, 2001, to Zethoff; U.S. Pat. No. 3,982,659 issued on Sep. 26, 1976, to Ross; U.S. Pat. No. 3,967,756 issued on Jul. 6, 1976, to Barish; U.S. Pat. No. 3,986,479, issued on Oct. 19, 1976, to Boedecker; U.S. Pat. No. 3,994,417 issued on Nov. 30, 1976, to Boedecker; U.S. Pat. No. 6,269,970 issued on Aug. 7, 2001, to Huang; U.S. Pat. No. 5,785,179 issued on Jul. 28, 1998, to Buczwinski; U.S. Pat. No. 5,366,104 issued on Nov. 22, 1994, to Armstrong; U.S. Pat. No. 5,322,178 issued on Jun. 21, 1994, to Foos; U.S. Pat. No. 5,050,737 issued on Sep. 24, 1991, to Josyln; U.S. Pat. No. 4,971,220 issued on Nov. 20, 1990, to Kaufman; U.S. Pat. No. 6,296,144 issued on Oct. 2, 2001, to Tanaka; U.S. Pat. No. 6,315,114 issued on Nov. 13, 2001, to Keck; U.S. Pat. No. 4,840,270 issued on Jun. 20, 1989, to Caputo; U.S. Pat. No. 4,471,881 issued on Sep. 18, 1984, to Foster; U.S. Pat. No. 5,647,506 issued on Jul. 15, 1997, to Julius; U.S. Pat. No. 6,401,968 issued on Jun. 11, 2002, to Huang; U.S. Pat. No. 6,269,969 issued on Aug. 7, 2001, to Huang; U.S. Pat. No. 6,412,634 issued on Jul. 2, 2002, to Telesca; U.S. Pat. No. 5,791,465 issued on Aug. 11, 1998, to Niki; U.S. Pat. No. 6,092,690 issued on Jul. 25, 2000, to Bitowft; and U.S. Pat. No. 6,092,690 issued on Jul. 25, 2000, to Bitowft; U.S. Patent Application Publication No. 2002/0064323 published on May 30, 2002, inventor Chin; and WO 00/27268 published on May 18, 2000, and assigned to The Procter & Gamble Co.; WO 02/14172 published on Feb. 21, 2002, and assigned to The Procter & Gamble Co.; and WO 99/55213 published on Nov. 4, 1999, and assigned to The Procter & Gamble Co.

EXAMPLES

Example 1

A disposable child sized cleaning implement comprising:
(a) a cleaning implement which is a 105 mm×140 mm rectangle comprising 60 gsm polyester nonwoven high loft batting material, Proef 1297 available from Libeltex of Meulebeke Belgium. The high loft batting material is releasably carrying the personal care composition, which comprises 50 gsm of a mixture of 0.001% by weight of lavender Oil with the remainder being BC20, the latter of which is available from Rhodia of France; and
(b) a child graphic disposed on the implement as illustrated in FIG. 5.

Example 2

A disposable child sized cleaning implement according to Example 1, except that the child graphic is that illustrated in FIG. 9.

Example 3

A disposable child sized cleaning implement according to Example 1, except that the cleaning implement is a two-layer laminate. The first layer of the laminate is a 40 gsm PET spunlace. While the second layer of the laminate is a 60 gsm polyester nonwoven high loft batting material, Proef 1297 available from Libeltex of Meulebeke Belgium. The high loft batting material is releasably carrying the personal care composition, which comprises 25 gsm of a mixture of 0.001% by weight of Chamomile Oil with the remainder being BC20, the latter of which is available from Rhodia of France.

Example 4

A disposable child sized cleaning implement according to Example 1, except that the personal care composition comprises 42 gsm of a composition as follows

| Component | % wt. |
| --- | --- |
| Sodium Laureth-3 Sulfate | 63.5 |
| Cocamidopropyl Betaine | 23.5 |
| PEG-200 Glyceryl Tallowate | 10.0 |
| Polyquaternium-10 | 1.0 |
| Preservative System | 0.5 |
| Whitener | 0.5 |
| Chamomile Oil | 0.001 |
| Balm Mint Oil | 0.001 |
| Perfume | 0.5 |
| Water | (Quantity sufficient to 100%) |

Example 5

A disposable child sized cleaning implement comprising:
(a) a cleaning implement which is a mitt and comprising a first member which is a 60 gsm polyester nonwoven high loft batting material, Proef 1297 available from Libeltex of Meulebeke Belgium, and a second member which is a three member laminate. The three member laminate contains a 90 gsm two layer stretch laminate, namely 259-50-3 available from Tredegar, of Richmond, Va. U.S.A., and a 30 gsm nonwoven, 008YLCO09U, available from BBA of Nashville Tenn., U.S.A. The high loft batting material is releasably carrying the personal care composition, comprises 85 gsm of a mixture of 0.0001% by weight of Sandalwood Oil with the remainder being BC20, the latter of which is available from Rhodia of France; and (b) a child graphic as illustrated in FIG. 6.

Example 6

Figure 21:
FIG. 21 illustrates another child graphic.
Figure 22:
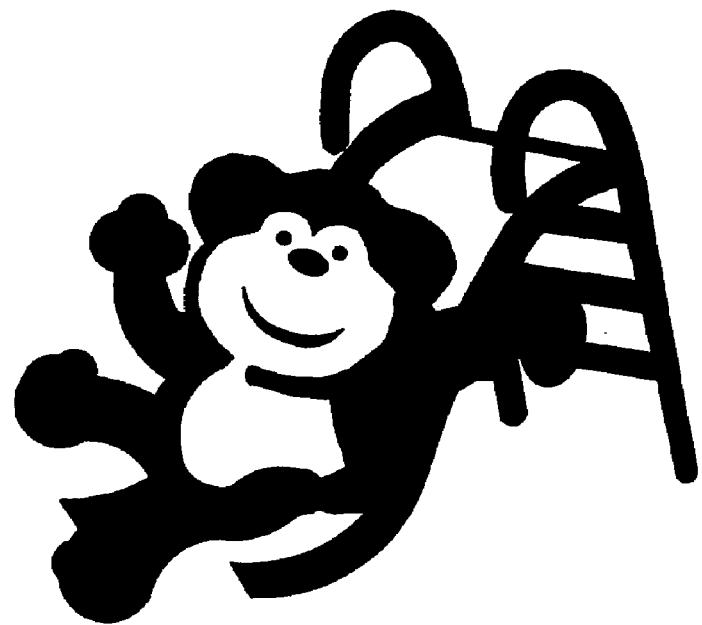
FIG. 22 illustrates another child graphic.

A disposable child sized cleaning implement according to Example 5, except that the child graphic is illustrated in FIG. 21.

Example 7

A disposable child sized cleaning implement according to Example 5, except that the child's cleansing mitt is the cleansing mitt of co filed application 60/453,167, filed on Mar. 10, 2003, entitled "Disposable Nonwoven Cleansing Mitt" in the name of Benjamin et al., (P&G Docket Number 9180PQ).

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable cleaning implement for bathing a child comprising:
   (a) a first member including a first periphery, the first member comprising a laminate of a nonwoven material layer and a high loft batting material layer;
   (b) a second member including a second periphery, the second member comprising a nonwoven, wherein the first and second members are positioned in an overlaying relationship and joined to one another about the first and second periphery to define an interior space for receiving a hand and an access opening for inserting a hand therein, and wherein at least one of the first and second members include a textured portion comprising raised and/or lowered portions;
   (c) between 1 g and 20 g of a personal care composition releasably carried by the cleaning implement, the personal care composition being at least partially disposed on the high loft batting material layer, the personal care composition comprising (i) a paste and/or a dry solid having less than 50% moisture content by weight of the personal care composition, (ii) a lathering surfactant, and (iii) one or more fragrances; and
   (d) one or more instructional child graphics disposed on the disposable cleaning implement wherein the one or more instructional child graphics comprises a character graphic and/or a child graphic related in subject matter to bathing.

2. The disposable cleaning implement of claim 1, wherein the instructional child graphic is in the form of one or more photographs, drawings, cartoons, symbols, or combinations thereof.

3. The disposable cleaning implement of claim 1, wherein the instructional child graphics are registered graphics.

4. The disposable cleaning implement of claim 1, wherein the cleaning implement is a mitt adapted to fit on the hand of a child.

5. The disposable cleaning implement of claim 4, wherein the mitt is thumb-less.

6. The disposable cleaning implement of claim 1, wherein the first and second members are joined together by a method selected from the group consisting of ultrasonic bonding, sewing, adhesive bonding, mechanical bonding, fusion bonding, heat bonding, thermal bonding, and combinations thereof.

7. The cleaning implement of claim 1, wherein the surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium monolauryl phosphate, sodium cocoglyceryl ether sulfonate, sodium $C_9$-$C_{22}$ soap, amine oxides such as lauramine oxide and cocoamine oxide, decyl polyglucose, lauryl polyglucose, sucrose cocoate, $C_{12-14}$ glucosamides, sucrose laurate, fatty amines, di-fatty quaternary amines, tri-fatty quaternary amines, imidazolinium quaternary amines, PEG 80 Sorbitan laurate, PEG-150 distearate, sodium laureth-13 carboxylate, disodium lauroamphodiacetate, sodium lauroamphoacetate, cetyl dimethyl betaine, cocoamidopropyl betaine, cocoamidopropyl hydroxy sultaine, and combinations thereof.

8. The disposable cleaning implement of claim 1, wherein the personal care composition further comprises one or more adjunct ingredients.

9. The disposable cleaning implement of claim 8, wherein the adjunct ingredient is selected from the group consisting of enzymes, absorbents, aesthetic components, pigments, colorings, colorants, skin sensates, anti-acne agents, anti-caking agents, antifoaming agents, preservative, conditioners, hair conditioners, dye, antimicrobial agents, glycerin, binders, buffering agents, bulking agents, chelating agents, solvents, cosmetic biocides, denaturants, external analgesics, film formers, humectants, polydimethylsiloxanes, Cyclic polyalkylsiloxanes, opacifying agents, pH adjusters, process aids, reducing agents, sequestrants, skin-conditioning and/or treating agents, moisturizers, aloe vera, hair detanglers, thickeners, hydrocolloids, zeolites, sugar amines and their salts, phytosterols, oxidants/radical scavengers, ascorbyl esters of fatty acids, ascorbic acid derivatives, plant extracts, fruit extracts, caffeine, candelilla wax, alpha-bisabolol, allantoin, glycyrrhetic acid, glycyrrhizic acid, abrasives, astringents, binders, gelling agents, thixatropic agents, sunscreen actives, vitamins, and combinations thereof.

10. An article of commerce comprising a container, said container housing one or more of said disposable cleaning implement of claim 1.

* * * * *